US008657445B2

United States Patent
Olsen

(10) Patent No.: US 8,657,445 B2
(45) Date of Patent: Feb. 25, 2014

(54) SYSTEM AND METHOD FOR DETERMINING AND PREDICTING IOL POWER IN SITU

(75) Inventor: Thomas Olsen, Århus C (DK)

(73) Assignee: IOL Innovations ApS, Arhus (DK)

( * ) Notice: Subject to any disclaimer, the term of this patent is extended or adjusted under 35 U.S.C. 154(b) by 183 days.

(21) Appl. No.: 13/063,326

(22) PCT Filed: Sep. 11, 2009

(86) PCT No.: PCT/DK2009/050236
§ 371 (c)(1),
(2), (4) Date: Jun. 23, 2011

(87) PCT Pub. No.: WO2010/028654
PCT Pub. Date: Mar. 18, 2010

(65) Prior Publication Data
US 2011/0242482 A1 Oct. 6, 2011

(30) Foreign Application Priority Data
Sep. 11, 2008 (DK) .............................. 2008 01272

(51) Int. Cl.
*A61B 3/00* (2006.01)
*A61B 3/10* (2006.01)
(52) U.S. Cl.
CPC ................................... *A61B 3/1015* (2013.01)
USPC ......................................................... 351/246
(58) Field of Classification Search
USPC .................. 359/205, 208, 212, 246
See application file for complete search history.

(56) References Cited

PUBLICATIONS

Olsen, T. "Calculation of intraocular lens power: a review." Acta Ophthalmol Scand. Aug. 2007;85(5):472-85. Epub Apr. 2, 2007.
Preussner, P.R., et al. "Ray tracing for intraocular lens calculation." J Cataract Refract Surg. Aug. 28, 2002 (8):1412-9.
Olsen, T. "On the Stiles-Crawford effect and ocular imagery."Acta Ophthalmol (Copenh). Feb. 1993;71(1):85-8.
Baker T Y. "Ray-tracing trough non-spherical surfaces." Proc Physical Soc (UK) 1943; (24): 361-364.
Binkhorst R D. "The optical design of intraocular lens implants." Ophthalmic Surg 1975; (6): 17-31.
Binkhorst R D. "Intraocular lens power." Int Ophthalmol Clin. 1979 Fall;19(3):83-94.
Binkhorst R D. "Intraocular lens power calculation." Int Ophthalmol Clin 1978; (19): 237-252.
Colenbrander M C. "Calculation of the power of an iris clip lens for distant vision." Br J Ophthalmol., 1973; (57): 735-740.
Connors R, III, et al. "Accuracy and reproducibility of biometry using partial coherence interferometry." J Cataract Refract Surg 2002; (28): 235-238.

(Continued)

*Primary Examiner* — Jack Dinh
(74) *Attorney, Agent, or Firm* — Dann, Dorfman, Herrell & Skillman; Robert C. Netter, Jr.

(57) ABSTRACT

The present invention relates to a system and a method for determining the power of an artificial intraocular lens (IOL) in situ. The invention furthermore relates to a system and a method for predicting the optical outcome of IOL surgery. Use of the system may provide prevention, treatment, or amelioration of diseases and disorders affecting the lens of the eye and which may benefit from IOL surgery. Moreover, the invention relates to a computer-readable medium for implementing such a system on a computer.

29 Claims, 7 Drawing Sheets

(56) References Cited

PUBLICATIONS

Drexler W., et al. "Partial coherence interferometry: a novel approach to biometry in cataract surgery." Am J Ophthalmol 1998; (126): 524-534.
Dubbelman M., et al. "The shape of the anterior and posterior surface of the aging human cornea." Vision Res 2006; (46): 993-1001.
Dubbelman M., et al. "Radius and asphericity of the posterior corneal surface determined by corrected Scheimpflug photography." Acta Ophthalmol Scand 2002; (80): 379-383.
Dunne M.C., et al. "Normal variations of the posterior corneal surface." Acta Ophthalmol (Copenh) 1992; (70): 255-261.
Findl O., et al. "Influence of operator experience on the performance of ultrasound biometry compared to optical biometry before cataract surgery." J Cataract Refract Surg 2003; (29): 1950-1955.
Fyodorov S.N., et al. "Calculation of the optical power of intraocular lenses." Invest Ophthalmol 1975; (14): 625-628.
Gernet H. "Intraocular lens planning. Geometric-optical and Sanders-Retzlaff-Kraff I and II formulas." Ophtalmologie 1990; (4): 96-101.
Vogel A., et al. "Reproducibility of optical biometry using partial coherence interferometry: intraobserver and interobserver reliability." J Cataract Refract Surg 2001; (27): 1961-1968.
Gullstrand A. The dioptrics of the eye. In: Helmholtz's Treatise on Physiological Optics. (Ed. Southall JPC). Optical Society of America, 1924; 351-352.
Haigis W. "Pseudophakic correction factors for optical biometry." Graefes Arch Clin Exp Ophthalmol., 2001; (239): 589-598.
Haigis W. The Haigis formula. In: Intraocular lens power calculations. (Ed.Shammas HJ). Slack Inc, 2004; 5-57.
Haigis W., et al. "Comparison of immersion ultrasound biometry and partial coherence interferometry for intraocular lens calculation according to Haigis Graefes." Arch Clin Exp Ophthalmol 2000; (238): 765-773.
Hoffer K.J. "The Hoffer Q formula: a comparison of theoretic and regression formulas." J Cataract Refract Surg 1993b; (19): 700-712.
Hoffer K.J. "Clinical results using the Holladay 2 intraocular lens power formula." J Cataract Refract Surg 2000; (26): 1233-1237.
Holladay J.T., et al. A three-part system for refining intraocular lens power calculations. J Cataract Refract Surg 1988; (14): 17-24.
Jansson F., et al. "Determination of the velocity of ultrasound in the human lens and vitreous." Acta Ophthalmol (Copenh) 1962; (40): 420-433.
Kiss B., et al. "Refractive outcome of cataract surgery using partial coherence interferometry and ultrasound biometry: clinical feasibility study of a commercial prototype II." J Cataract Refract Surg 2002; (28): 230-234.
Olsen T. "On the calculation of power from curvature of the cornea." Br J Ophthalmol 1986a; (70): 152-154.
Olsen T. "Prediction of intraocular lens position after cataract extraction." J Cataract Refract Surg 1986b; (12): 376-379.
Olsen T. "Theoretical approach to intraocular lens calculation using Gaussian optics." J Cataract Refract Surg 1987a; (13): 141-145.
Olsen T. "Theoretical vs empirical prediction of aphakic refraction." Arch Ophthalmol 1987b; (105): 1042-1045.
Olsen T. "Theoretical, computer-assisted prediction versus SRK prediction of postoperative refraction after intraocular lens implantation." J Cataract Refract Surg 1987c; (13): 146-150.
Olsen T. "On the Stiles-Crawford effect and ocular imagery." Acta Ophthalmol (Copenh) 1993; (71): 85-88.
Olsen T. The Olsen formula. In: Intraocular lens calculations. (Ed. Shammas HJ). Thorofare, NJ: Slack Inc, 2004; 27-40.
Olsen T. "Prediction of the effective postoperative (intraocular lens) anterior chamber depth." J Cataract Refract Surg 2006b; (32): 419-424.
Olsen T. "Calculation of intraocular lens power: a review." Acta Ophthalmol Scand 2007; (85): 472-485.
Olsen T., et al. "We don't need fudge factors in IOL power calculation." Eur J Implant Refract Surg 1993; (5): 51-54.
Olsen T., et al. "Intraocular lens power calculation with an improved anterior chamber depth prediction algorithm." J Cataract Refract Surg 1995; (21): 313-319.
Olsen T., et al. "Phacoemulsification, capsulorhexis, and intraocular lens power prediction accuracy." J Cataract Refract Surg 1993; (19): 695-699.
Olsen T., et al. "Prediction of postoperative intraocular lens chamber depth." J Cataract Refract Surg 1990a; (16): 587-590.
Olsen T., et al. "Prediction of pseudophakic anterior chamber depth with the newer IOL calculation formulas." J Cataract Refract Surg 1992; (18): 280-285.
Olsen T., et al. "Theoretical versus SRK I and SRK II calculation of intraocular lens power." J Cataract Refract Surg 1990b; (16): 217-225.
Olsen T., et al. "Accuracy of the newer generation intraocular lens power calculation formulas in long and short eyes." J Cataract Refract Surg 1991; (17): 187-193.
Olsen T., et al. "Calibration of axial length measurements with the Zeiss IOLMaster." J Cataract Refract Surg 2005a; (31): 1345-1350.
Packer M., et al. "Immersion A-scan compared with partial coherence interferometry: outcomes analysis." J Cataract Refract Surg 2002; (28): 239-242.
Preussne P., et al. "Ray tracing for intraocular lens calculation." J. Cataract Refract. Surg., 2002, 28:1412-19.
Retzlaff J. "A new intraocular lens calculation formula." J Am Intraocul Implant Soc 1980; (6): 148-152.
Retzlaff J.A., et al. "Development of the SRK/T intraocular lens implant power calculation formula." J Cataract Refract Surg 1990; (16): 333-340.
Sanders D., et al. "Comparison of the accuracy of the Binkhorst, Colenbrander, and SRK implant power prediction formulas." J Am Intraocul Implant Soc 1981; (7): 337-340.
Sanders D.R., et al. "Comparison of the SRK II formula and other second generation formulas." J Cataract Refract Surg 1988; (14): 136-141.
Sanders D.R., et al. "Comparison of the SRK/T formula and other theoretical and regression formulas." J Cataract Refract Surg 1990; (16): 341-346.
Stiles W.S., et al. "The luminous efficiency of rays entering the eye pupil at different points." Proc Roy Soc (London) B 1933; (1 12): 428-450.

SYSTEM AND METHOD FOR DETERMINING AND PREDICTING IOL POWER IN SITU

This is a national stage application of PCT/DK2009/050236 filed on Sep. 11, 2009, which claims priority to Denmark (DK) patent application PA 2008 01272, filed on Sep. 11, 2008. The entire disclosure of each of the foregoing applications is incorporated by reference herein.

The present invention relates to a system and a method for determining the power of an artificial intraocular lens (IOL) in situ. The invention furthermore relates to a system and a method for predicting the optical outcome of IOL surgery. Use of the system may provide prevention, treatment, or amelioration of diseases and disorders affecting the lens of the eye and which may benefit from IOL surgery. Moreover, the invention relates to a computer-readable medium for implementing such a system on a computer.

BACKGROUND OF INVENTION

During cataract surgery (and other lens surgery) the ophthalmic surgeon extracts the biological crystalline lens and replaces it with an artificial intraocular lens (IOL). If the optical properties of the artificial implant match the optical properties and the dimensions of the eye, the patient has a good chance that the vision after surgery can be good without needing spectacles, irrespective of the need for spectacles before surgery. FIG. 20 shows a schematic diagram of the human eye wherein the various anatomical parts and structures are indicated. FIG. 1 shows a simple model of the human eye. The refraction of light through the eye takes place in 1) the cornea and 2) the lens in order to focus the light at 3) the retina at the back of the eye. If there is an imbalance between any of the ocular components, the eye will need a spectacle correction to see clearly. FIG. 2 shows the phakic eye (top half) and the pseudophakic eye (bottom half). In the phakic eye the natural crystalline lens 22 is present. In the pseudophakic eye the natural crystalline lens has been substituted with a synthetic lens 23, typically an IOL implant. In the aphakic eye no lens is present.

Cataract is one of the leading causes of blindness and the surgical treatment of cataract is one of the most commonly performed surgical procedures world-wide. In recent years the overall improvement in safety and efficacy of lens surgery and the development of a number of new IOL designs have broadened the indication for lens surgery to encompass not only patients with cataract, but also patients with refractive problems like myopia (nearsightedness) hypermetropia (shortsightedness) and presbyopia (spectacle dependency in reading).

The aim of any IOL power calculation formula is to control the optical outcome of lens surgery. Because all presently available formulas use non-realistic models for the optics of the eye they require a number of corrective terms to be calculated in retrospect from observed data in order to work accurately. Examples of these 'fudge' factors include the 'A-constant' (SRK-formula), 'Surgical Factor' (Holladay) or 'effective ELP or ACD' (Hoffer or Binkhorst fomula). The effect of these 'fudge' factors is to correct for any off-set errors arising in the formula by applying an average corrective term making the predictions accurate in the average case.

When trying to predict the outcome of IOL surgery an accurate model of the eye is crucial. But no matter how precise and detailed the model of the eye ends up being, the position of the IOL in the eye cannot be measured before surgery and therefore has to be estimated. And without an exact knowledge of the final postoperative position of the IOL the postoperative refraction of the eye cannot be predicted substantially detailed to provide uncorrected vision for any patient who undergoes IOL surgery.

In the growing field of refractive lens surgery where patient demand and expectations are increasing, the surgeon may sometimes be faced with the problem that the patient ended up with an unexpected refractive result. Most of the times a review of the preoperative measurements may identify a measurement error as the cause of this 'refractive surprise'. In other cases the reason for the wrong IOL power may not be evident, and the possibility of a formula error or a mislabelled IOL should be considered.

SUMMARY OF INVENTION

Before doing an IOL exchange it might be helpful to verify the power of the IOL in situ to facilitate the selection of a more appropriate IOL power. In the past, methods to verify the IOL power in situ have been based on measurements of the Purkinje-Sanson III+IV images reflected from the anterior and posterior surface of the IOL (Holladay et al., 1985, Binkhorst et al., 1987, Olsen, 1988). Although such methods have proven highly accurate they are not easy to perform as they require special equipment not within the normal clinical techniques. Thus, an object of the invention is to calculate the power of an IOL in situ based on normal clinical measuring techniques.

This is achieved by a system for determining the postoperative power of an intraocular lens (IOL) in an eye of a patient (i.e. IOL power in situ), said IOL having known power and geometry, said system comprising:
  a) means for obtaining, measuring and/or calculating at least one of the following parameters of the pseudophakic eye of the patient: the axial length, the postoperative anterior chamber depth, corneal radius and the diameter of the pupil,
  b) means for performing a ray tracing analysis of an optical model of the pseudophakic eye at least partly based on the parameters obtained in step a), and
  c) means for calculating the IOL power in situ at least partly based on the ray tracing analysis performed in step b).

The invention further relates to a method for determining the postoperative power of an intraocular lens (IOL) in an eye of a patient, said IOL having known power and geometry, said method comprising the steps of:
  a) obtaining, measuring and/or calculating at least one of the following parameters of the pseudophakic eye of the patient: the axial length, the postoperative anterior chamber depth, corneal radius and the diameter of the pupil, and
  b) ray tracing analysis of an optical model of the pseudophakic eye at least partly based on the parameters obtained in step a),
  whereby the IOL power in situ is calculated.

Thus, this first embodiment of the invention provides a system and a method for measuring IOL power in situ. The IOL power will typically be known from data provided by the IOL manufacturer, i.e. the measured IOL power in situ can be verified against the known IOL power thereby verifying that the method based on clinical measurements in situ is correct. IOL power may also be termed "dioptric power of IOL" and will typically be measured in dioptres (also termed diopters).

A further object of the invention is to control the refractive outcome of IOL surgery (e.g. spectacle dependence) and thereby provide better vision after surgery, where uncorrected vision is the optimal goal, e.g. avoiding the use of spectacles.

This is achieved by a system for preoperatively predicting the optical properties (i.e. refractive outcome) of a pseudophakic eye of a patient with an IOL of known power and geometry, said system comprising:
  a) means for providing statistical analysis of clinical data from a plurality of eye operated patients,
  b) means for calculating, obtaining and/or measuring at least one of the following parameters of the phakic eye of the patient: the axial length, the preoperative anterior chamber depth, the corneal radius, the diameter of the pupil and the lens thickness,
  c) means calculating the expected postoperative position of the IOL in the pseudophakic eye of the patient based on the statistical analysis from step a) and the parameters of the phakic eye of the patient provided in step b), and
  d) means for performing ray tracing analysis of a model of the pseudophakic eye, and
  e) means for calculating the IOL power in situ at least partly based on the ray tracing analysis performed in step d).

The invention further relates to a method for preoperatively predicting the optical properties of a pseudophakic eye of a patient with an IOL of known power and geometry, said method comprising the steps of:
  a) statistical analysis of clinical data from a plurality of eye operated patients,
  b) calculating, obtaining and/or measuring at least one of the following parameters of the phakic eye of the patient: the axial length, the preoperative anterior chamber depth, the corneal radius, the diameter of the pupil and the lens thickness,
  c) calculating the expected postoperative position of the IOL in the pseudophakic eye of the patient based on the statistical analysis from step a) and the parameters of the phakic eye of the patient provided in step b), and
  d) ray tracing analysis of a model of the pseudophakic eye, said ray tracing analysis at least partly based on the expected postoperative position of the IOL obtained in step d), whereby the IOL power in situ is calculated,
  thereby predicting the optical properties of the pseudophakic eye of the patient prior to surgery.

According to the system and method in this invention, the physical measurements of the human eye, including the measurement of the axial length and the physical position of the IOL, can be correctly interpreted and analyzed by ray tracing techniques to accurately reflect the ocular imagery and thereby be used to calculate the optical properties of the IOL.

On a general level the invention is based on a logical "circle" around the crucial issue:

How to predict the postoperative position of an IOL in the eye of a patient.

The first part of this logical circle is a new method whereby the IOL power in situ is calculated based on a measurement of the postoperative anterior chamber depth. The calculated IOL power in situ can then be verified against the known IOL power.

In the second part this new method is used for the reverse calculation, i.e. predicting the postoperative anterior chamber depth (before surgery) by knowing the IOL power and geometry, data which is typically provided by IOL manufacturers.

The third part is a verification of the reverse calculation based on clinical measurements on a substantial number of patients that have had eye surgery.

And once the postoperative anterior chamber depth can be predicted prior to surgery the optical properties of a specific IOL in a specific eye can be predicted (fourth part).

Thus, the circle is closed because initially (first part) it was shown that IOL power in situ can be calculated when the postoperative chamber depth is known. Thereby the refractive outcome of IOL surgery can be predicted.

Treatment

In further embodiments the present invention can provide the means and methods for the prevention, treatment and/or amelioration of diseases and/or disorders which are related to the lens of an eye and which may benefit from IOL surgery. The method comprises the prediction of the optical properties of a specific IOL in a specific eye thereby controlling the outcome of refractive IOL surgery. The means provide a system for performing the method upon the lens to be treated, and means such as software which enables the system to perform the method of above.

Thus, an object of the present invention is a system which may be used for the prevention, treatment and/or amelioration of diseases and/or disorders which are related to the lens and which may benefit from IOL surgery by predicting the optical properties of a specific IOL in a specific eye, thereby controlling the outcome of refractive IOL surgery.

Individual to be Treated

The lens, and thus the eye of an individual to be treated may be any animal or human being. The method is generally practiced on a living eye of an animal or a human being. Preferably the individual to be treated is a mammal, such as but not limited to a dog, cat, primate, horse, cow or human being. Most preferably the herein disclosed method is used for the treatment of a lens of a human being.

Thus, a further aspect of the invention relates to system for prevention, treatment and/or amelioration of a disease and/or disorder which is related to a lens of an eye of a patient and which may benefit from IOL surgery, said system comprising:
  i) means for providing an IOL of known power and geometry,
  ii) means for calculating and evaluating the refractive outcome if said IOL were to be inserted in said eye of said patient, said calculation based on any of the herein listed methods,
  iii) means for repeating steps i) and ii) until a satisfactory refractive outcome has been obtained for a specific IOL, and
  iv) means for inserting/implanting said specific IOL in the eye of the patient.

The invention further relates to a method for prevention, treatment and/or amelioration of a disease and/or disorder which is related to a lens of an eye of a patient and which may benefit from IOL surgery, said method comprising the steps of:
  i) providing an IOL of known power and geometry,
  ii) calculating and evaluating the refractive outcome if said IOL were to be inserted in said eye of said patient, said calculation based on any of the herein listed methods,
  iii) repeating steps i) and ii) until a satisfactory refractive outcome has been obtained for a specific IOL, and
  iv) inserting/implanting said specific IOL in the eye of the patient.

The diseases and/or disorders may be selected from: presbyopia; cataract at all stages; opacities, brunescence or cloudiness of the lens; refractive errors; myopia; hyperopia and astigmatism.

The invention furthermore includes a computer program product having a computer readable medium, said computer program product comprising means for carrying out any of the listed methods.

DETAILED DESCRIPTION OF THE INVENTION

Difference Between Existing Methods and the Present Invention

The present invention differs from the prior art in that
1) the position of the IOL within the eye is based on a true, physically defined postoperative anterior chamber depth rather than a virtual postoperative anterior chamber depth (or ELP), and
2) a realistic model is provided for the optics of the eye with an accurate and correct interpretation of the measured data.

Characterising and Modelling the Eye

Performing a precise ray tracing analysis of the optical properties of an eye requires a correct model of the eye. When light passes through the ocular media, light is refracted at a number of interfaces or surfaces. In a preferred embodiment of the invention the model of an eye used in the ray tracing analysis contains at least one of the following surfaces and/or interfaces: the anterior cornea surface, the posterior cornea surface, the anterior and posterior lens surfaces of the biological lens, the IOL anterior surface, the IOL posterior surface and the retina.

A crucial parameter for a correct model of the eye is the axial length of the eye. Various clinical methods exist for measuring the axial length, such as ultrasound which have been used widely for many years. However, optical coherence interferometry has lately proven to be highly accurate and in a preferred embodiment of the invention the axial length of an eye is measured by means of optical partial coherence interferometry, which has been made commercially available as the IOLMaster instrument from Carl Zeiss Meditec AG, Germany and recently as the Lenstar LS 900 instrument from Haag-Streit AG, Switzerland.

However, in the correct interpretation of the readings of the Zeiss IOLmaster or the Lenstar LS 900 instruments, it should be realized that the output reading of the Zeiss IOLMaster and the Lenstar LS 900 has been calibrated against axial length measurements obtained by immersion ultrasound. This has been done in order not to change the world of known IOL power calculation formulas based on ultrasound. It is possible, however, to back-calculate the physical distance measured by the Zeiss IOLMaster or Lenstar LS 900 by numerical constants to provide the correct and true axial length of an eye (the optical path length).

Thus, in a preferred embodiment of the invention the true axial length of an eye is expressed as $AL_{True}=(AL_{Zeiss}*K_1+K_2)*K_3/K_4$ where $AL_{Zeiss}$ is the axial length output from a Zeiss IOLMaster or Lenstar LS 900 instrument and $K_1$, $K_2$, $K_3$ and $K_4$ are numerical constants and $K_4$ is the refractive index of the eye.

Preferably $K_1$ is between 0.86 and 1.06, such as between 0.89 and 1.03, such as between 0.91 and 1.01 such as between 0.93 and 0.99, such as between 0.94 and 0.98, such as between 0.95 and 0.97, such as between 0.952 and 0.96. In the preferred embodiment of the invention $K_1=0.9571$.

Preferably $K_2$ is between 1.2 and 1.4, such as between 1.23 and 1.37, such as between 1.26 and 1.34 such as between 1.28 and 1.31, such as between 1.29 and 1.3, such as between 1.295 and 1.309, such as between 1.3 and 1.306. In the preferred embodiment of the invention $K_2=1.3033$.

Preferably $K_3$ is between 1.25 and 1.45, such as between 1.28 and 1.42, such as between 1.31 and 1.39 such as between 1.33 and 1.37, such as between 1.34 and 1.36, such as between 1.347 and 1.359, such as between 1.353 and 1.357. In the preferred embodiment of the invention $K_3=1.3549$.

Preferably $K_4$ is between 1.26 and 1.46, such as between 1.29 and 1.43, such as between 1.32 and 1.4 such as between 1.35 and 1.37, such as between 1.356 and 1.366, such as between 1.359 and 1.363, such as between 1.361 and 1.362. In the preferred embodiment of the invention $K_4=1.3616$.

Furthermore, the radius of the anterior surface of the cornea is preferably measured by means of keratometry and/or by means of corneal topography. It is furthermore assumed that the radius of the posterior surface of the cornea is a fixed ratio of the radius of the anterior surface of the cornea. The radius of the posterior surface of the cornea is preferably assumed to be $C_{p-a}$ times the radius of the anterior surface of the cornea, where $C_{p-a}$ is a numerical constant. Preferably $C_{p-a}$ is between 0.7 and 1, such as between 0.75 and 0.95, such as between 0.8 and 0.9, such as between 0.81 and 0.88, such as between 0.82 and 0.86, such as between 0.83 and 0.85. In the preferred embodiment of the invention $C_{p-a}=0.84$.

A correct model of the eye is only provided if the asphericity of the corneal surfaces is accounted for. The asphericity of the posterior corneal surface is preferably assumed to be linearly dependent on the anterior surface and the asphericity of the posterior and the anterior corneal surfaces are preferably assumed to be depending on the age of the patient. More specifically the asphericity of the anterior corneal surface is preferably assumed to be $X_1$ plus $X_2$ times the age of the patient, and the asphericity of the posterior corneal surface is preferably assumed to be $X_1$ plus $X_3$ times the asphericity of the anterior corneal surface minus $X_4$ times the age of the patient where $X_1$, $X_2$, $X_3$ and $X_4$ are numerical constants.

Preferably $X_1$ is between 0.7 and 0.82, such as between 0.71 and 0.81, such as between 0.72 and 0.8, such as between 0.73 and 0.79, such as between 0.74 and 0.78, such as between 0.75 and 0.77, such as between 0.755 and 0.765. In the preferred embodiment of the invention $X_1=0.76$.

Preferably $X_2$ is between 0.002 and 0.004, such as between 0.0022 and 0.0038, such as between 0.0024 and 0.0036, such as between 0.0026 and 0.0034, such as between 0.0028 and 0.0032, such as between 0.0029 and 0.0031, such as between 0.00295 and 0.00305. In the preferred embodiment of the invention $X_2=0.003$.

Preferably $X_3$ is between 0.25 and 0.4, such as between 0.27 and 0.38, such as between 0.29 and 0.36, such as between 0.3 and 0.35, such as between 0.31 and 0.34, such as between 0.32 and 0.33, such as between 0.322 and 0.327. In the preferred embodiment of the invention $X_3=0.325$.

Preferably $X_4$ is between 0.0062 and 0.0082, such as between 0.0064 and 0.008, such as between 0.0066 and 0.0078, such as between 0.0068 and 0.0076, such as between 0.007 and 0.0074, such as between 0.0071 and 0.0073, such as between 0.00715 and 0.00725. In the preferred embodiment of the invention $X_4=0.0072$.

Spherical aberration is a phenomenon of many lenses including the cornea and non-aspheric IOLs where peripheral rays are refracted differently from central rays. The human eye has a certain amount of positive spherical aberration which accounts for the 'night myopia' that many people experience at mesopic (dim light) conditions where the pupil becomes large. Spherical aberration is corrected somewhat by the so-called Stiles-Crawford effect, whereby the retinal sensitivity is depending on the angle by which the rays hit the retina. The Stiles-Crawford effect predicts the retinal sensitivity to be at a maximum for rays entering the pupil centre and to be of less efficiency for rays entering the pupil edge. The consequence of the Stiles-Crawford effect is that it tends to correct for the effect of spherical aberration when the pupil becomes large. In a preferred embodiment of the invention the IOL power is corrected for spherical aberration, preferably by means of the Stiles Crawford effect $I=I_0\exp(-C*\gamma^2)$, where C is a numerical constant and $\gamma$ is the distance from the centre of the pupil. $\gamma$ is measured in mm.

Preferably C is between 0.06 and 0.16, such as between 0.07 and 0.15, such as between 0.08 and 0.14, such as between 0.09 and 0.13, such as between 0.1 and 0.12, such as between 0.104 and 0.114, such as between 0.106 and 0.11. In the preferred embodiment of the invention C=0.108.

In a preferred embodiment of the invention the diameter of the pupil is assumed to be 3 mm. However, in a further embodiment the pupil diameter is measured for every patient.

In order to calculate IOL power in situ or predict the optical outcome of an IOL to be implanted, it is crucial to know the physical properties and dimensions of the IOL. IOL manufacturer's typically provide data for the refractive index and the thickness and the curvatures of the front and back surfaces of the IOL, and the power and geometry are preferably calculated from these data (Labelled power is by ANSI-definition the power which can calculated from the central, paraxial radii using a 'thick-lens vergence-based model)'. Furthermore, the exact curvatures of the anterior and posterior surfaces of the IOL are preferably calculated from the manufacturer's data for labelled power, anterior radii and posterior radii of the IOL. Sometimes however, the IOL manufacturers consider the IOL data as proprietary information.

It should be stressed that similar results and accuracy for calculating the IOL power in situ has not been published before. The present method of accurately interpreting the clinical data from eye measurements, building a realistic non-corrected model of the eye and performing ray tracing analysis based in this model leads to an previously unknown accuracy in determining the IOL power in situ. As will be shown in example 3 the present method leads to an accuracy of 0.66 D in determining the IOL power in situ for a large range of labelled IOL powers. This is a clear improvement compared to previous methods, such as the "thick lens" method.

Predicting Outcome of IOL Surgery

One embodiment of the invention relates to predicting the optical outcome of eye surgery and the first step is to predict the postoperative position of the IOL after implantation. The hypothesis is that the IOL position must be depending on various physical characteristics of the eye. To verify this hypothesis a plurality of patients with an actual IOL implant has been characterized before and after surgery in terms of various measurable physical parameters that are thought to influence the position of the IOL. A statistical analysis, such as a multiple regression analysis or a multivariate analysis, of these physical parameters can reveal whether they are somehow related. If so, formulas that express one of the measured parameter as a function of other measured parameters can be provided and more specifically, the postoperative position of the implant can be expressed as a formula depending of physical parameters that can be provided prior to surgery. Thus, characterising a patient in terms of various physical parameters prior to surgery should provide a qualified value for the specific postoperative position of the IOL in the eye of that patient.

However, even if the postoperative position of the IOL can be predicted prior to surgery, nothing is gained in terms of predicting the optical outcome prior to IOL surgery unless a correct model of the eye is provided and a substantially accurate method is provided to analyse the refraction of light in the eye model. Thus, second step is to provide a detailed and correct model of the eye and the IOL implant, i.e. correctly interpreting the various measurable physical parameters, the optical and physical properties of the plurality of interfaces and surfaces in the eye and so on.

The third step is then to analyse the refraction of light inside the eye to finally predict the optical outcome of the IOL implant prior to surgery.

In a further aspect of the invention the age of the patient is included when the expected postoperative anterior chamber depth is obtained and/or calculated. When humans and animals age, small changes are induced in the eyes, whereby the position of an IOL implant in the eye will somehow depend on the age of the patient or animal.

The current method uses a statistical approach to describe a relationship between various clinical measurements on a plurality of eye operated patients. A plurality of parameters have been obtained, measured and/or calculated on the patients before and/or after IOL surgery, such as preoperative refractive properties, postoperative refractive properties, axial length of the eye, preoperative anterior chamber depth, postoperative anterior chamber depth, average corneal radius, diameter of the pupil and lens thickness. Furthermore, the age of the patients was preferably registered.

The Position of the IOL

When the plurality of eye operated patients are characterized, the position of the IOL implant after surgery can be provided by measuring the postoperative anterior chamber depth of the eye, e.g. by various clinical measuring techniques. The preoperative and the postoperative anterior chamber depths can be measured by means of ultrasound and/or by means of optical techniques, such as partial coherence interferometry or Scheimpflug imaging. Alternatively, the effective postoperative anterior chamber depth can be obtained by ray tracing analysis of the eye based on the various physical eye parameters and the measured postoperative refractive properties of the eye. E.g. by computer iteration, solving for the postoperative anterior chamber depth that predicted the actual measured postoperative refraction within a small limit, i.e. ±0.01 D (spherical equivalent) using the ray tracing technique.

In a preferred embodiment of the invention, the statistical analysis on the plurality of eye operated patients comprises the step of calculating the mean value of at least one of the following parameters relating to the plurality of eye operated patients: postoperative anterior chamber depth, axial length, preoperative anterior chamber depth, lens thickness, corneal radius, pupil diameter and the age of the patients.

In one embodiment of the invention multiple regression analysis is applied to the data of the plurality of eye operated patients, whereby the expected postoperative position of the IOL can be expressed as a function of at least one of the following parameters: mean postoperative chamber depth ($ACD_{post, mean}$), preoperative anterior chamber depth ($ACD_{pre}$), mean anterior chamber depth ($ACD_{pre, mean}$), axial length (Ax), mean axial length ($Ax_{mean}$), corneal radius (CR), mean corneal radius ($CR_{mean}$), lens thickness (LT), mean lens thickness ($LT_{mean}$), age (Age) and mean age ($Age_{mean}$).

In a further embodiment of the invention the expected postoperative anterior chamber depth ($ACD_{post, exp}$) is expressed as:

$$ACD_{post, exp} = ACD_{post, mean} + C_1*(Ax-Ax_{mean}) + C_2*(ACD_{pre}-ACD_{pre, mean}) + C_3*(CR-CR_{mean}) + C_4*(LT-LT_{mean}) + C_5*(Age-Age_{mean}),$$

wherein $C_1$, $C_2$, $C_3$, $C_4$ and $C_5$ are numerical constants provided by the multiple regression analysis.

When the IOL design is changed as a result of new developments and/or the surgical technique is changed it may change the average position of the IOL in the eye after surgery. In those instances it may be necessary to study the surgical outcome of a number of cases in order to have a statistically reliable estimate of the average IOL position or the ACD. Thus, a further object of the invention is to facilitate new IOL designs and/or surgical techniques, preferably by continuously incorporating new results in the statistical formulas.

Therefore: In one embodiment of the invention the mean postoperative chamber depth ($ACD_{post, mean}$) is continuously adjusted to reflect any changes in IOL design and/or surgical techniques. More specifically, the mean postoperative chamber depth ($ACD_{post, mean}$) can be adjusted according to the following formula:

$$ACD_{post, mean} = ACD_{post} - C_1*(Ax - Ax_{mean}) - C_2*(ACD_{pre} - ACD_{pre, mean}) - C_3*(CR - CR_{mean}) - C_4*(LT - LT_{mean}) - C_5*(Age - Age_{mean}),$$

where $C_1$, $C_2$, $C_3$, $C_4$ and $C_5$ are the numerical constants provided by the multiple regression analysis.

If the age is measured in years and anterior chamber depth, axial length, corneal radius and length thickness are measured in millimeters, the values of the numerical constants $C_1$, $C_2$, $C_3$, $C_4$ and $C_5$ may be in the below indicated intervals. Measuring clinical parameters in other units (such as inches) will lead to a numerical correction of the numerical constants.

Preferably $C_1$ is between 0.06 and 0.16, such as between 0.07 and 0.15, such as between 0.08 and 0.14, such as between 0.09 and 0.13, such as between 0.10 and 0.12, such as between 0.103 and 0.113, such as between 0.105 and 0.107. In the preferred embodiment of the invention $C_1 = 0.1059$.

Preferably $C_2$ is between 0.26 and 0.36, such as between 0.27 and 0.35, such as between 0.28 and 0.34, such as between 0.29 and 0.33, such as between 0.3 and 0.32, such as between 0.304 and 0.312, such as between 0.306 and 0.31. In the preferred embodiment of the invention $C_2 = 0.308$.

Preferably $C_3$ is between −0.48 and −0.38, such as between −0.47 and −0.39, such as between −0.46 and −0.4, such as between −0.45 and −0.41, such as between −0.44 and −0.42, such as between −0.437 and −0.427, such as between −0.434 and −0.43. In the preferred embodiment of the invention $C_3 = -0.432$.

Preferably $C_4$ is between 0.14 and 0.24, such as between 0.15 and 0.23, such as between 0.16 and 0.22, such as between 0.17 and 0.21, such as between 0.18 and 0.20, such as between 0.187 and 0.197, such as between 0.19 and 0.194. In the preferred embodiment of the invention $C_4 = 0.1918$.

Preferably $C_5$ is between −0.0045 and −0.0025, such as between −0.0043 and −0.0027, such as between −0.0041 and −0.0029, such as between −0.0039 and −0.0031, such as between −0.0037 and −0.0033, such as between −0.0036 and −0.0034, such as between −0.00355 and −0.00345. In the preferred embodiment of the invention $C_5 = -0.0035$.

In order to evaluate the result of a ray tracing analysis and thereby assess the optical properties of an eye, at least one point spread function is preferably calculated and evaluated at the retina of the eye and/or at the point of best focus.

DRAWINGS

Figure 7:
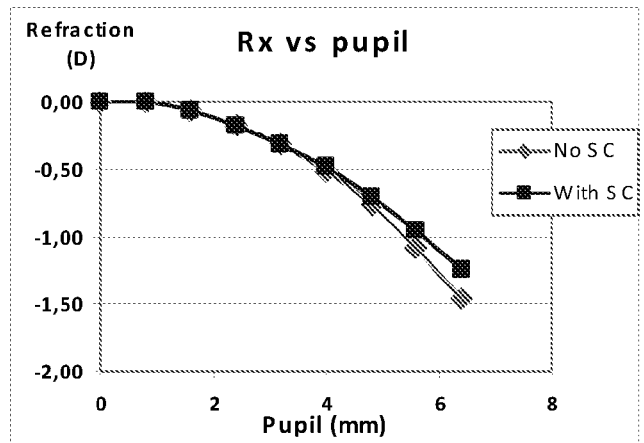

FIG. 7 illustrates the effect of pupil size on the refraction predicted for a normal eye of average dimension with a spherical IOL implant. As the pupil widens the eye becomes myopic as a result of spherical aberration. The effect is compensated for by the Stiles-Crawford effect ('SC').

Figure 8:
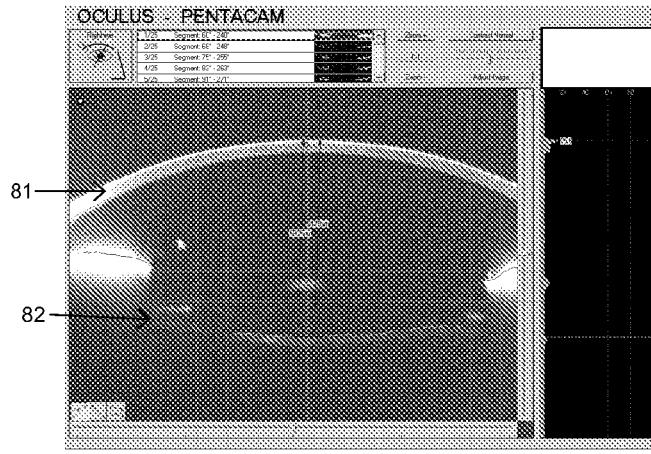

FIG. 8 shows the position of the IOL determined from a Scheimpflug image of the anterior segment of a newly operated patient.

Figure 9:
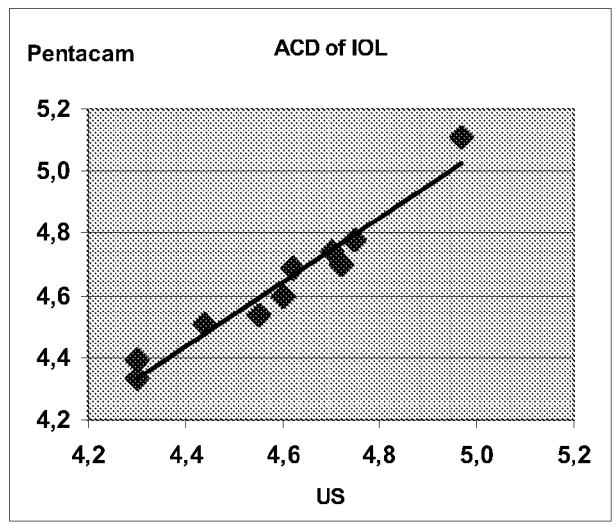

FIG. 9 shows the postoperative ACD measured in 10 cases by ultrasound (US) as well as by Scheimpflug (Pentacam) photography, respectively.

Figure 10:
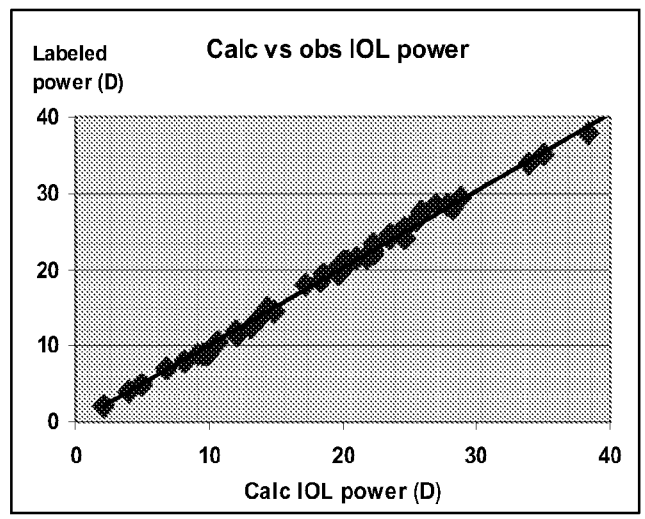

FIG. 10 shows the IOL power calculated by ray tracing plotted against the labelled power in 53 eyes.

Figure 11:
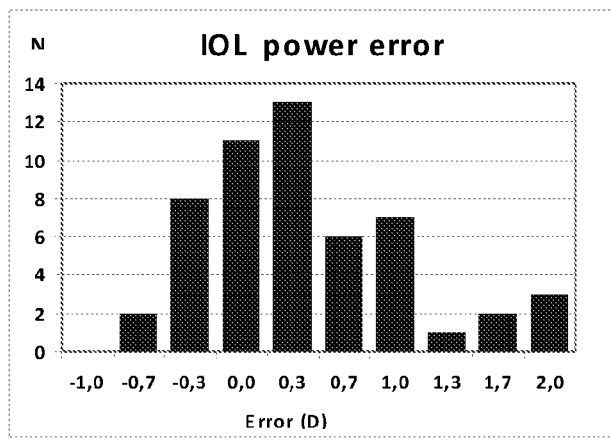

FIG. 11 shows the difference between the calculated and the labelled IOL power in 53 eyes with a known IOL implant.

Figure 12:
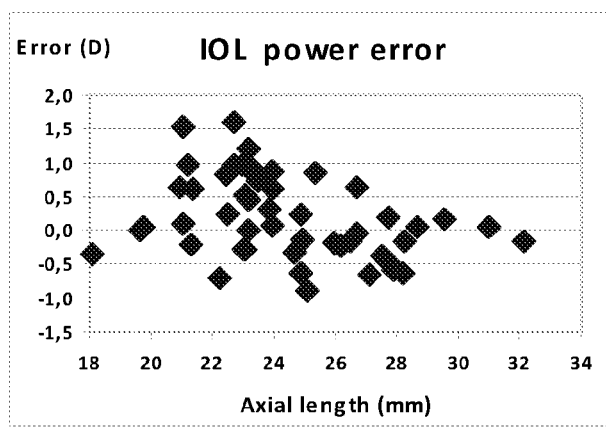

FIG. 12 shows the difference between the calculated and the labelled IOL power in 53 eyes plotted against the axial length of the eye.

Figure 13:
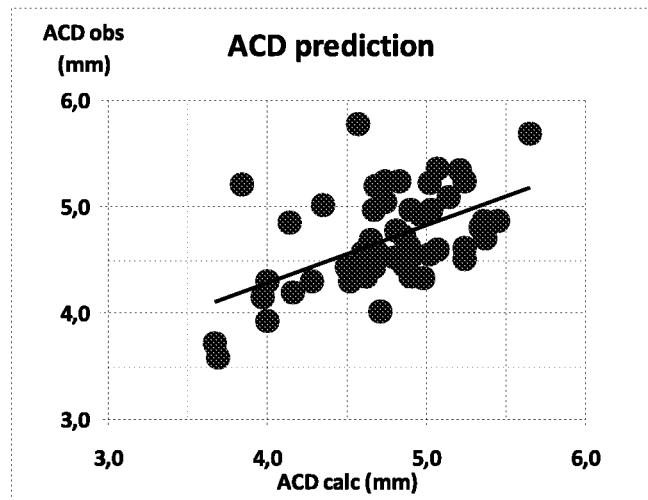

FIG. 13 shows the calculated ACD plotted against the measured ACD in 53 eyes with a known IOL implant.

Figure 14:
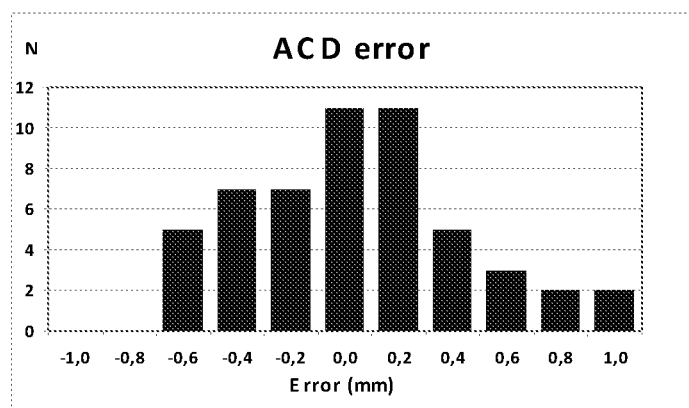

FIG. 14 shows the difference between the calculated and the measured ACD in 53 eyes with a known IOL implant.

Figure 15:
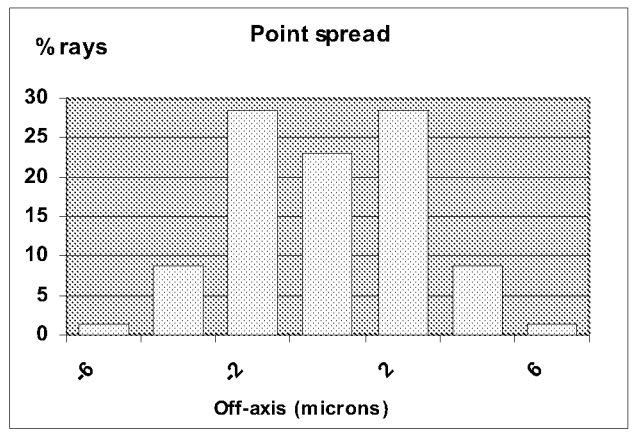

FIG. 15 shows the point spread function of case shown in table 7 for which the minimum blur (RMS) was found. The RMS was in this case found to be 0.0289.

Figure 16:
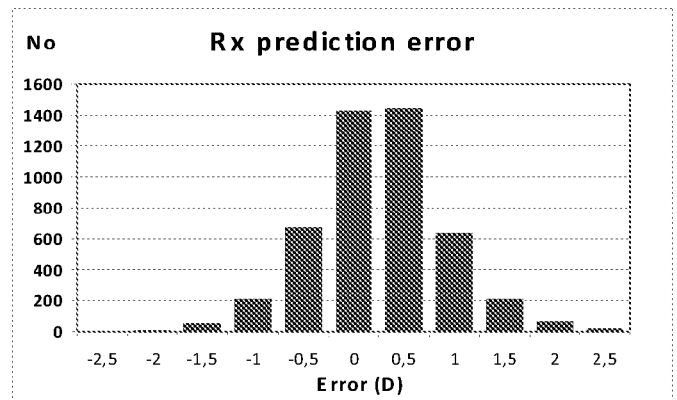

FIG. 16 shows the distribution of the prediction error, defined as the difference (O-E) between the observed and the expected refraction in 4479 IOL implant cases.

Figure 17:
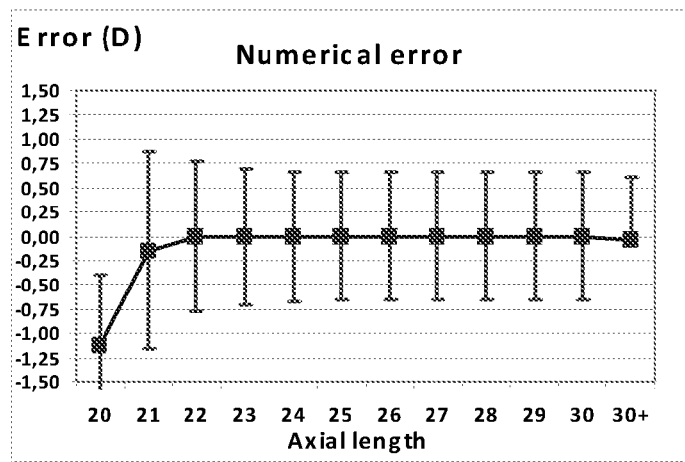

FIG. 17 shows the prediction error plotted against the axial length of 4479 eyes. Apart from the group of very short eyes (n=8), no significant bias with the axial length was observed.

Figure 18:
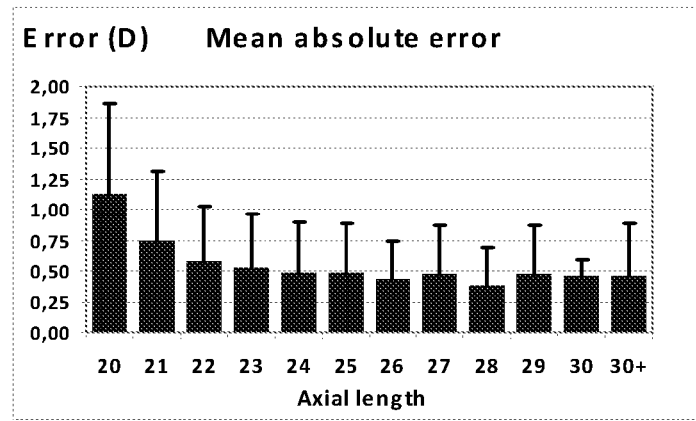

FIG. 18 shows the mean absolute error, defined as the absolute value of the difference (O-E) between the observed and the expected refraction in 4479 IOL implant cases.

Figure 19:
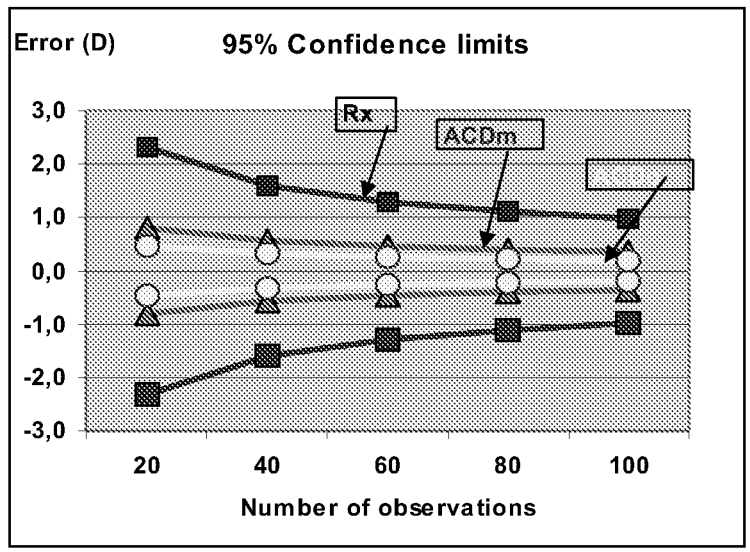

FIG. 19 illustrate confidence limits for the estimation of IOL constants (in SRK A-constant IOL power equivalent units) according to 3 different methods used on the content of table 3+8.

Figure 20:
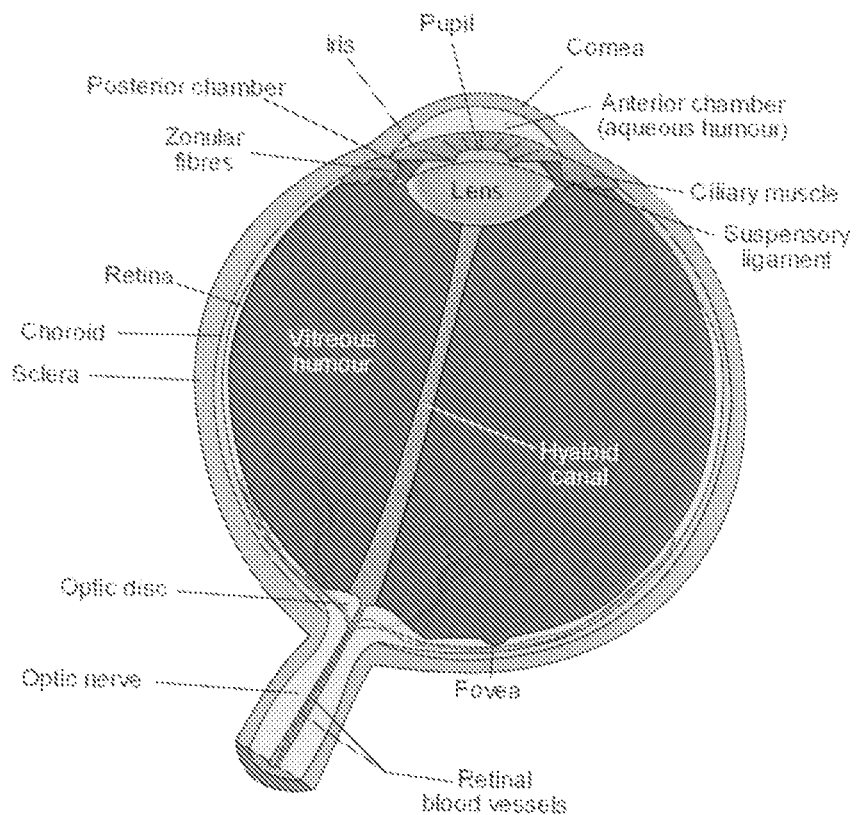

FIG. 20 is an illustration of an eye found on Wikipedia.

BACKGROUND

Early Theoretical Formulas

Since the introduction of artificial intraocular lenses in the 1970's, several methods have been described to calculate the dioptric power of the IOL implanted during lens surgery. The first methods used optical formulae known from the optical-physical theory of 'thin lenses'. These methods were simple formulas based on the assumptions that 1) the cornea was a 'thin lens' the power of which could be measured,
2) the IOL was also a 'thin lens' of known effective power,
3) the position of the IOL was assumed to be fixed, and
4) the distance from the surface of the eye (the cornea) to the back surface of the eye (the retina) was a distance that could be measured by clinical methods.

With some variation, the format of these early 'thin lens' IOL power calculation formulas can be described as (Olsen, 2007):

$$P_0 = \frac{n_2}{(Ax-d)} - \frac{1}{\left(\frac{1}{K} - \frac{d}{n_1}\right)}$$

where K=power of the cornea in dioptres, d=distance from cornea to effective lens plane of the IOL (also called the anterior chamber='ACD'), $n_1$=refractive index for the ACD, Ax=axial length of the eye (distance from cornea surface to retina), $n_1$=refractive index of medium behind the IOL (the vitreous cavity) and $P_0$=power in dioptres of the IOL needed to produce emmetropia (unaided distance vision) after surgery.

Examples of the 'thin lens' formulas included Colenbrander (Colenbrander, 1973), Fyodorov (Fyodorov et al., 1975), Binkhorst (Binkhorst, 1975, Binkhorst, 1979), Gernet (Gernet, 1990) Hoffer (Hoffer, 1993a, Hoffer, 2000), Holladay (Holladay et al., 1988).

Behind the simple format of the abovementioned 'thin lens' IOL power calculation equation there are however several unknowns that should be dealt with in order to work in clinical practice. Some of these unknowns include which refractive index to use, how to accurately calculate the corneal power, the correction of principal planes of a 'thick lens' model, the accuracy of the axial length measurements, how to transform ultrasound measurements into optically meaningful distances, how to deal with higher-order aberrations and especially: how to predict the effective lens plane of the implant.

Because of the great number of unknowns, all the available formulas described today require the use of corrective terms and personalization factors to adjust the formula to real clinical life.

The Empirical Formulas

Soon after the introduction of the early theoretical formulas the clinical experience showed however the accuracy of these formulas to be inferior to the accuracy of the so-called 'empirical formulas'. The latter formulas used a statistical (linear multiple regression) approach to describe a linear relationship between the clinical measurements and the dioptric power of the IOL needed for emmetropia.

The most important example of the regression methods is the so-called SRK (Sanders-Retzlaff-Kraff) formulas (Retzlaff, 1980, Sanders et al., 1981, Sanders et al., 1988, Retzlaff et al., 1990, Sanders et al., 1990), which were based on the statistical analysis of a large number of cases with preoperative measurements of the corneal power (the 'K-reading'), the axial length of the eye as determined by ultrasound (the 'A-scan'), the actual implant power and the observed refraction (the spectacle correction).

The original SRK I formula was a simple linear regression equation (Retzlaff, 1980) as follows: $P_0$=A−0.9K−2.5Ax, where $P_0$=power of implant for unaided distance vision ('emmetropia'), K=dioptric reading of keratometer (using index 1.3375), Ax=axial length of the eye as measured by ultrasound and A=the 'A-constant' depending on the type of the IOL and the surgical technique. The idea of the 'A-constant' was that this constant was a 'black-box' constant capable of absorbing any off-set errors in the system, including differences in IOL type, placement in the eye, surgical and measuring techniques. To overcome systematic off-set errors it was recommended to 'personalize' the 'A-constant' according to the surgeon's own technique.

The success of the original SRK I-formula and the later versions (SRK II, SRK /T) was due to fact that it was based on empirical data and therefore could be made to work without systematic errors in the average case. However, because the formula was based on statistical analysis the predictive value has been shown to be of lower value in unusual eyes like long and short eyes, eyes with steep or flat corneas and in eyes with ametropia (Olsen, 1987c, Olsen, 1987b, Olsen et al., 1990b, Olsen et al., 1991). Furthermore, because it was purely dependent on the empirical data including the measuring technique it was not easy to use in different clinical environment with differences (and possible improvements) in surgical or measurement technique, first of all the measurement of axial length.

Recent Developments

One of the most important components of any optical formula relating to IOL implants, is the prediction of the position of the implant after surgery.

With the exception of the Olsen formula (Olsen, 1987a, Olsen, 1987c, Olsen et al., 1990b, Olsen et al., 1991, Olsen and Corydon, 1993, Olsen and Gimbel, 1993, Olsen, 2004) all the current IOL power calculation formulas methods use virtual models for the position of the IOL after surgery, where the position of the IOL is described not as a physical, measurable distance but rather as a 'effective lens position' (ELP) defined as the distance from the corneal surface to effective lens plane of the IOL, assuming 'thin lens' calculations.

For many years the Olsen formula has been the only formula using a 'thick lens' approach, which means that the cornea and the IOL were treated like a 'thick lens' of finite thickness with exact correction of principal planes. The idea of a 'thick lens' calculation, as first advocated by Olsen (Olsen, 1987a), was that the position of the IOL was defined as a physical measurable distance, which eventually could be verified by clinical methods. Many improvements in IOL power calculations formula deal with improved algorithms for the prediction of the $ACD_{post}$ (Olsen, 1986b, Holladay et al., 1988, Olsen et al., 1990a, Olsen et al., 1992, Hoffer, 1993b, Olsen et al., 1995, Haigis, 2004, Olsen, 2006b).

However, although a 'thick lens' model is superior to a 'thin lens' model with a more realistic representation of the position of the IOL in the eye the 'thick lens' model still assumes spherical surfaces of the optical system. Because neither the cornea nor the IOL are necessarily spherical, a better model might be based on exact ray tracing, which can be made to work on any surface type. The ray tracing technique forms the basis of the present concept.

Clinical Measuring Techniques

The eye is not a simple physical lens system but rather a biological organ, the structure of which can be measured only by clinical methods. In order to determine the IOL power, the optical components of the eye must be evaluated. Important components are:

1. The optics of the cornea
2. The length of the eye
3. The anterior chamber depth Corneal Optics The refractive power of the cornea is usually provided by measuring the curvature of the front surface of the cornea by an instrument called the 'keratometer'. What is actually measured is the magnification of the convex mirror constituted by the anterior reflecting surface of the eye. This is converted into radius assuming the central portion of the cornea is spherical. When the keratometer reports the 'power' of the cornea it does so by assuming the cornea is a 'thin lens' with a single refracting surface of power:

$$F = \frac{n_2 - n_1}{r}$$

where F=refractive power of surface in dioptres, r=radius of curvature in meters, $n_1$=refractive index of first media (air=1.0) and $n_2$=refractive index of second media (cornea).

The conventional calibration of clinical keratometers assumes the refractive index of the single-surfaced cornea to be 1.3375, giving the equation:

$$D = \frac{337.5}{r}$$

where D=power of the cornea in dioptres, r=radius of curvature in millimeters.

As shown by the inventor (Olsen, 1986a), the refractive index calibration of 1.3375 is not accurate from a more physiological, 'thick lens' theory, which predicts the corneal power to be about 0.75 D lower in the average case. This 'inborn error' of the common keratometer reading is important from a physical point of view because if not corrected for, it will induce an error in all subsequent calculations and eventually require a correction at the end to work in an IOL power formula.

Another problem deals with the topographical variation in corneal radius that may be found not only in normal corneas but especially in corneas that have had previous refractive surgery (PRK, LASIK, LASEK and other laser ablation procedures with the aim to correct the refractive error by changing the curvature of the anterior surface). In such corneas the shape of the anterior surface is far from spherical, and may need to be evaluated using corneal topography measuring the curvature in numerous points of the entire corneal surface.

In order to treat the cornea as a 'thick lens' the corneal thickness and the curvature of the posterior surface also need to be taken into consideration. In most corneal models the posterior curvature is assumed to be a fixed ratio of the anterior curvature assuming a standard corneal shape. For many years the standard shape and hence the radius of the posterior surface was assumed to be as proposed by Gullstrand (Gullstrand, 1924). However, it is not until recently that more modern studies have provided detailed information not only on the curvatures of both surfaces of the cornea, but also on their asphericity (Dunne et al., 1992, Dubbelman et al., 2002, Dubbelman et al., 2006). These findings have improved the conditions to build more realistic models for the optics of the cornea and hence the entire ocular optics The refractive index of the cornea is assumed to be a constant value of 1.376 and the thickness of the cornea is assumed to be a constant value of 0.5 mm. The anterior curvature is assumed to be measured using conventional keratometry and/or by corneal topography. However, the radius reading is used rather than the diopter reading.

The posterior surface of the cornea is assumed to be a fixed ratio of the anterior surface according to the model described by Dubbelman (Dubbelman et al., 2002) so that:

$$R_2 = 0.84 * R_1$$

where $R_2$=radius of posterior surface of the cornea and $R_1$=radius of anterior surface of the cornea.

Also from the work of Dubbelman (Dubbelman et al., 2002) the asphericity of the corneal surfaces is assumed to depend on the age of the patient according to the following equations:

$$K_a = 0.76 + 0.003 * \text{Age}.$$

$$K_p = 0.76 + 0.325 * K_a - 0.0072 * \text{Age}$$

where $K_a$=asphericity of the anterior surface of the cornea, $K_p$=asphericity of the posterior surface of the cornea and Age=age of the patient in years.

The Dubbelman model used here predicting the posterior central curvature of the cornea to be 84% of the anterior curvature differs from the previous Gullstrand ratio of 6.8/7.7 (88.3%) used by Olsen in the original 'thick lens' formula. If not for the asphericity this would mean that the corneal power is lower than previously assumed. However, when the asphericity of the cornea is also taken into account the effective power of the cornea has been shown to be surprisingly close to the power predicted by the thick lens formula using the original Gullstrand ratio (Olsen, 2007).

Length of the Eye ('Axial Length').

Ultrasound

The axial length of the eye is a very important variable that needs to be measured with a high accuracy. An error of 1 mm in the axial length transposes into a 2.5 D error in the spectacle plane in the average eye. The axial length has traditionally been measured by ultrasound using so-called 'A-scan'. What is actually measured is the transit time of ultrasound as it travels through the ocular media and reflects at the internal boundaries of the eye. Assuming a known velocity of ultrasound in the different ocular compartments (cornea, anterior chamber, lens and vitreous compartment) it is possible to calculate the distance from the cornea to the acoustically reflecting membrane at the back of the eye.

There are a number of uncertainties in the measurement of the axial length by ultrasound. Firstly, the velocity of ultrasound has to be known accurately in the different ocular media. This need not be the case considering the varying cataract density seen in clinical practice. Secondly, many ultrasound techniques use applanation of the cornea to transmit the ultrasound to the eye and this may cause indentation of the cornea during measurement and shortening of the reading. Thirdly, ultrasound measures the distance to the reflecting membrane at the back surface of the eye (presumably the internal limiting membrane constituting the boundary between the vitreous cavity and the nerve fiber layer of the retina), which is not identical to the position of the light absorbing retinal photoreceptors of the eye.

The fact that there is an intrinsic error of the ultrasound measurement due to the difference between point of measurement and the position of the effective focal plane at the retina (=the photoreceptors), has led many IOL power calculation formulas to incorporate a corrective term called 'the retinal thickness', typically around 0.25 mm.

Optical Biometry

In recent years the introduction of laser biometry using partial coherence interferometry (PCI) (Drexler et al., 1998) has significantly improved the accuracy by which the axial length can be measured. The PCI technique has been made commercially available as the IOLMaster© instrument made by Carl Zeiss Meditec©, Jena, Germany and recently also as the Lenstar LS 900© instrument made by Haag-Streit AG, Switzerland. The wavelength of light is much shorter than that of sound which greatly improves the physical resolution. While typical precision values with good ultrasound measurements are stated to be within ±0.1 mm, the precision with PCI is stated to be approximately ten-fold better, i.e. within ±0.01 mm and it is independent on the observer (Connors, III et al., 2002, Findl et al., 2003, Haigis, 2001, Kiss et al., 2002, Packer et al., 2002, Vogel et al., 2001). Furthermore, the fact that the retinal pigment epithelium is the end point of optical measurement makes the measurements by the PCI technique optically more correct (and longer than that of ultrasound).

However, just like measurements using ultrasound are dependent on the assumed ultrasound velocity, optical biometry is dependent on the assumed group refractive indices of the phakic eye ('Phakic'—the state of an eye that still has its natural (crystalline) lens intact). The indices used by the Zeiss IOLMaster© were estimated by Haigis (Haigis, 2001) partly based on extrapolated data. As shown by the inventor, however, the index calibration of the phakic eye may need adjustment to give consistent readings between the preoperative and the postoperative readings (Olsen and Thorwest, 2005a).

For an accurate interpretation of the axial length reading of the Zeiss IOLMaster© or the Lenstar LS 900 it should be realized that the output reading of these machines are not the true optical path length of the eye, i.e. it is not the true axial length. In order not to change the world of A-constants and other formula constants used for years with ultrasound, the readings given by the commercial version of the Zeiss IOLMaster© or the Lenstar LS 900 were calibrated against immersion ultrasound according to the following formula (Haigis et al., 2000, Haigis, 2001):

$$Ax_{Zeiss}(OPL/1.3549-1.3033)/0.9571$$

where $Ax_{Zeiss}$ is the output reading of the Zeiss or Lenstar LS 900 instrument and OPL is the optical path length measured by PCI. Thus, $$OPL=(Ax_{Zeiss}*0.9571+1.3033)*1.3549$$

Assuming a refractive index of 1.3574 for the phakic eye (Haigis, 2001):

$$Ax_{true}=(Ax_{Zeiss}*0.9571+1.3033)*1.3549/1.3574$$

According to Olsen (Olsen and Thorwest, 2005b) the refractive index of 1.3574 for the phakic eye should be replaced by the index 1.3616 giving the true axial length from the Zeiss reading according to:

$$Ax_{true}=(Ax_{Zeiss}*0.9571+1.3033)*1.3549/1.3616$$

This conversion is preferably used in the present approach.

Measuring the anterior Chamber Depth—ACD

The measurement of the anterior chamber depth (definition used here: distance from corneal surface to anterior surface of the lens being natural or articifial) can be made with ultrasound or with optical techniques. What is measured by ultrasound is the transit time for ultrasound to travel from the corneal surface to the anterior surface of the lens where the beam is reflected. As is the case for the measurement of the axial length there are some disadvantages of this technique, including the possible indentation of the cornea during measurement and uncertainty regarding the velocity of ultrasound assumed for the conversion of transit time to distance.

Optical techniques include measurement of the visible depth of the anterior chamber as seen in the slit lamp (microscope with slit illumination often used in ophthalmological examinations), and more recently measurements using PCI (Zeiss ACMaster©) or Scheimpflug imaging of the anterior segment of the eye (example of manufacturer: Pentacam© by Oculus Inc). These methods may be regarded as more reliable than ultrasound as they do not need to touch the eye and use optical principles for the distance measurements.

Optical Model

Ray Tracing

The present approach uses exact ray tracing to simulate the optical properties of the eye. This method is well known from physical science and uses Snell's law of refraction:

$$\frac{Sin\theta_1}{Sin\theta_2} = \frac{n_2}{n_1}$$

where $\theta_1$=angle of incidence of incoming light in first media, $\theta_2$=angle of refracted light in second media, $n_1$=refractive index of first media and $n_2$=refractive index of second media.

Knowing the curvatures of each surface of a given optical system it is possible to simulate the imagery by 'firing' a number of rays through the system and observe the distribution of the rays at the image plane. A later example illustrates how this can be done.

The present approach assumes rotational symmetry of the individual surfaces and assumes the rays are equally distributed over the area of the entrance aperture.

The mathematics involved in the ray tracing methodology is well known from optical engineering and involves the description of ellipses and conicoid sections (Baker, 1943).

IOL Model

The physical description of the IOL studied in this application was based on the manufacturer's data on the refractive index, the thickness and curvatures of front and back surfaces of the IOL. The surface curvatures vary according to the power of the implant so it was necessary to use tabulated values of the physical data as a function of labelled power.

By definition (ANSI-standard), the labelled power of an IOL refers to the paraxial curvatures of the lens. In case of a spherical IOL this curvature is constant over the entire area. In case of an aspheric IOL the curvature is depending on the asphericity and varies from the central to the peripheral parts of the lens.

Prediction of IOL Position (ACD) After Surgery

Figure 1:
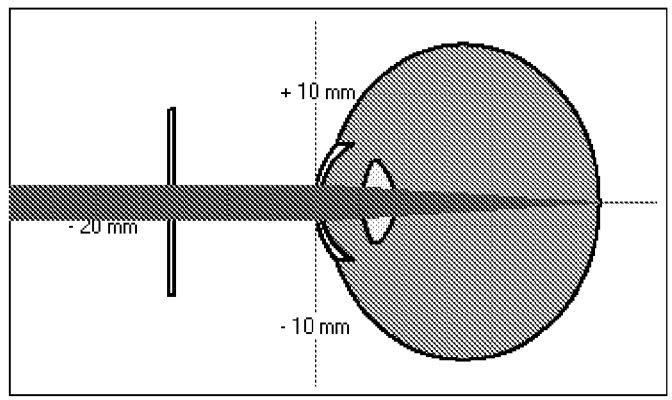
FIG. 1 is a model of an eye showing the refraction of light.
Figure 2:
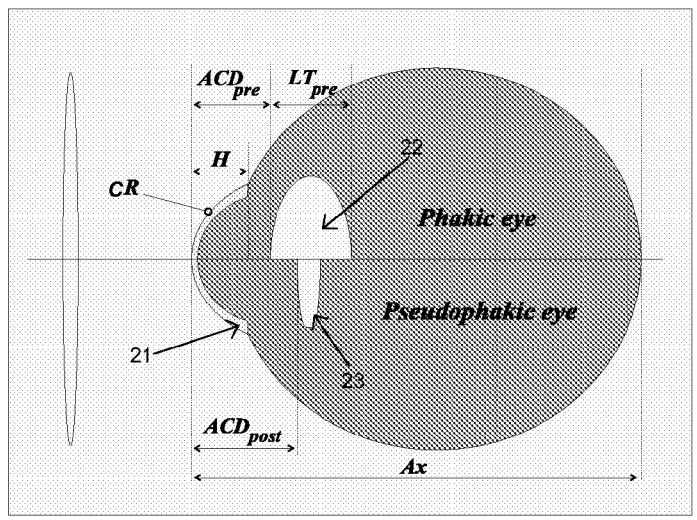
FIG. 2 illustrates the ocular components of the eye before and after surgery.

At the time of the early theoretical formulas very little was known about the actual position of the implant after surgery. For example the Binkhorst I formula (Binkhorst, 1979) used a fixed value of the ELP to predict the effective position of the implant in each case. Today there is accumulating evidence that the ELP (or the ACD) is not a fixed value but depends on the dimensions of the eye. Among the factors are the preoperative length of the eye (Ax), the preoperative anterior chamber depth ($ACD_{pre}$), the lens thickness and the corneal radius. FIG. 2 shows the ocular components of the eye before surgery ('phakic eye'—upper part) and after surgery ('pseudophakic eye'—lower part) with important variables used in the prediction of the position of the implant. 'Ax'=axial length, '$ACD_{pre}$'=preoperative ACD, 'LT'=lens thickness, 'CR'=front radius of cornea 21, 'H'=corneal height,. '$ACD_{post}$'=postoperative anterior chamber depth.

Spherical Aberration and the Stiles-Crawford Correction

Figure 6:
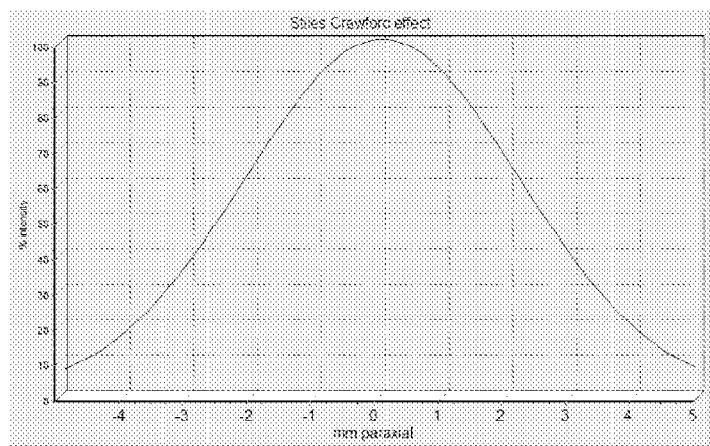
FIG. 6 illustrates the Stiles-Crawford effect showing the retinal sensitivity as a function of the distance from the central axis (x-axis in this figure but y-axis in the ray tracing scheme (FIG. 3)).

In the foregoing section, the optics of the eye has been described as a system of combined lenses and it has been assumed that all rays are of equal significance for the image to the picked up by the retina. This need not be the case, however. Due to the existence of the so-called Stiles-Crawford effect (Stiles W S and Crawford B H, 1933) the retinal sensitivity is depending on the angle by which the rays hit the retina. The Stiles-Crawford effect predicts the retinal sensitivity to be at a maximum for rays entering the pupil centre and to be of less efficiency for rays entering the pupil edge. The Stiles-Crawford effect may be expressed as:

$$I = I_0 \exp(-0.108 * \gamma^2),$$

where γ=distance from the centre of the pupil in mm. FIG. 6 illustrates the Stiles-Crawford effect showing the retinal sensitivity as a function of the distance from the central axis (x-axis in this figure but y-axis in the ray tracing scheme).

The consequence of the Stiles-Crawford effect is that is tends to correct for the effect of spherical aberration when the pupil becomes large (Olsen, 1993). Spherical aberration is a phenomenon of many lenses including the cornea and non-aspheric IOL's, where peripheral rays are refracted more and brought to a focus at a shorter focal length than central rays. The spherical aberration of the human eye is real and accounts for the 'night myopia' that many people experience at mesopic (dim light) conditions where the pupil becomes large.

Spherical aberration is not taken into account when the optics are described according to 'thin lenses' or 'thick lenses' but is readily demonstrated using ray tracing. Another advantage of ray tracing is that the Stiles-Crawford effect can also be incorporated by giving each ray a weight according to the Stiles-Crawford function.

Improving the Empirical Procedures to Estimate the IOL Constants

When the IOL design is changed as a result of new developments or the surgical technique is changed it may change the average position of the IOL in the eye after surgery. In those instances it may be necessary to study the surgical outcome of a number of cases in order to have a statistically reliable estimate of the average IOL position or the ACD.

According to previous formulas (e.g. the SRK formula) the recommended procedure is to study the average refractive outcome of a representative number of patients with a given IOL implant, and from the observed prediction error adjust the IOL constant to improve the outcome in future cases.

The conventional method involves the statistical analysis of the actual refractive outcome of a number of cases. The following example shows how this can be done according to the SRK I formula (rearranged):

$$A = P_0 + 0.9K + 2.5Ax$$

where $P_0$=power of implant giving emmetropia, K=dioptric reading of keratometer (using index 1.3375), Ax=axial length of the eye. The implant power giving emmetropia can be estimated from the actual refraction according to the 'rule of thumb':

$$P_0 = P_1 + 1.5Rx$$

where $P_1$=power of implant actually implanted and Rx=refraction obtained with this IOL power. So, if a patient with a 21.5 D implant ended up with −1.0 D spectacle correction, the $P_0$ is 20.0 D.

The statistical error (±SD) associated with the estimation of the 'A-constant' is typically around 1.4 D (Olsen, 2007), meaning that in order to be within ±0.25 D (95% confidence limits) the number of observations must be greater than 100 cases.

The present approach differs in that it is based on direct measurements and/or calculations of the postoperative ACD in a representative number of patients and this value is used directly to adjust the average IOL position. I.e. the present approach requires no other empirical constants than the aver-age postoperative anterior chamber depth $ACD_{post, mean}$. This will be demonstrated in a later example.

If the eye model is correct it should be possible to predict the optical properties of the eye with an IOL implant from the optical result of the operation. Thus, by measuring the refractive outcome (the obtained spectacle correction), the postoperative ocular dimensions, including the position of the IOL, it should be possible to predict the power of the IOL actually implanted and/or its position within the eye (the ACD).

EXAMPLES

In the above, the invention has been explained in detail with reference to specific embodiments and as illustrated in figures and drawings. In the following the invention will be explained with reference to specific examples. It will be obvious to the skilled person, that the invention may be performed in many other forms and variations and should not be limited to specific embodiments or examples.

Example 1

Ray Tracing Analysis of Gullstrand Eye

The exact schematic eye of Gullstrand (Gullstrand, 1909, Gullstrand, 1924) was used as an example of the ray tracing analysis. For many years the exact schematic eye of Gullstrand has been used to simulate the optical properties of the human eye. Apart from the object plane and the image plane the structure of the schematic eye is a 6 surface model as shown in Table 1:

TABLE 1

Surfaces of the exact schematic eye of Gullstrand.

| Surface | Name | x-Position | Radius | Conic | index |
|---|---|---|---|---|---|
| 0 | Object | −30 | 10000 | 0 | 1 |
| 1 | Cornea front | 0 | 7.7 | 0 | 1.38 |
| 2 | Cornea back | 0.5 | 6.8 | 0 | 1.34 |
| 3 | Lens front | 3.6 | 10 | 0 | 1.39 |
| 4 | Nucleus front | 4.15 | 7.91 | 0 | 1.41 |
| 5 | Nucleus back | 6.57 | −5.76 | 0 | 1.39 |
| 6 | Lens back | 7.2 | −6 | 0 | 1.34 |
| 7 | Retina (image) | 24 | −13 | 0 | 0 |

Each surface is given number from left to right, a name, an axis location (x-Position), a radius of curvature (positive means anterior convex and negative means anterior concave), a conic coefficient (zero for this eye model) and a refractive index.

Figure 3:
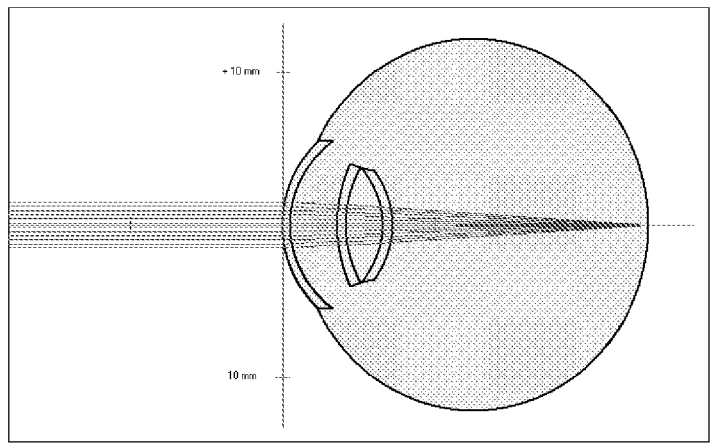
FIG. 3 illustrates a ray tracing example of Gullstrand schematic eye.

In the Gullstrand eye the axial length of the eye is assumed to be 24.00 mm, which is the location of the retina where the image is perceived. An example of a ray trace of this eye, the structure of which is listed in Table 1, is shown in FIG. 3 for an entrance beam width of 3 mm with a limited number of incoming parallel rays. Rays are assumed to origin at infinity and being refracted at each surface according to Snell's law of refraction until they hit the posterior surface of the eye (the retina).

When using a sufficient number of rays (>1000 or more) the distribution of the ray intersections on the x-axis can be studied to give an estimate of the effective focus along the visual axis. In the example shown in FIG. 3 the paraxial focus is at 24.385 mm, the effective focus is at 24,161 mm and the marginal focus is at 24.065 mm. Likewise the distribution of the ray intersections with the retina (which can be regarded as a slightly curved y-axis) can also be studied. The latter distribution is known in optical terms as the point-spread function ('PSF'), which is a measure of the image quality. As a measure of the spread it is common practice to calculate the root-mean-square ('RMS') of the distances from the axial focus.

Figure 4:
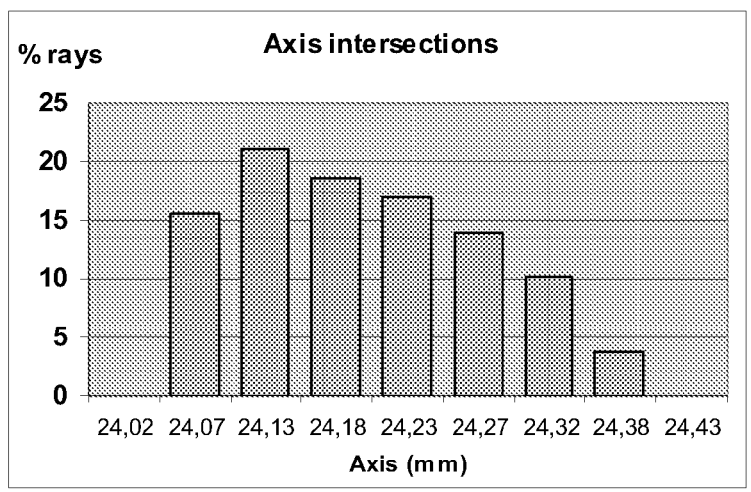
FIG. 4 shows the distribution of ray intersections with the axis for the Gullstrand eye assuming an entrance pupil of 3 mm.

In FIG. 4 is shown the distribution of the x-axis ray intersections (number of rays=1000) for the Gullstrand eye assuming a pupil of 3 mm. It is noted that all rays in the ray tracing example of FIG. 3 are brought to a focus behind the retina at 24.0 mm. The eye in FIG. 3 is therefore slightly longsighted (hyperopic).

Figure 5:
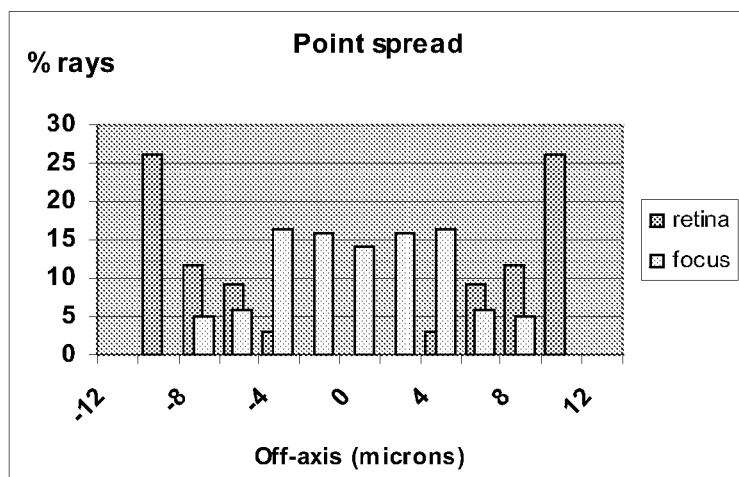
FIG. 5 shows the point spread function of the Gullstrand eye at the retina (dark columns) and at the best focus 0.194 mm behind the retina (light columns).

The analysis of the point-spread-function in the y-direction was provided at two planes: 1) at the retina and 2) at the best focus, which was found by computer iteration to locate about 0.194 mm behind the retina. FIG. 5 illustrates the point spread function of the Gullstrand eye at the retina (dark columns) and at the best focus 0.194 mm behind the retina (light columns). The corresponding RMS was found to be 0.256 and 0.109 at the retina and at the best focus, respectively.

In conclusion, this example has shown that the quality of the image giving the least blur would be enhanced if the axial length of the eye had been 0.194 mm longer or, alternatively, if a small spectacle correction with a power of about +0.5 D (equivalent value of shift in axial length) had been placed in front the eye.

Example 2

Ray Tracing Analysis of Eye with IOL Implant

Further ray tracing examples show an eye of average dimension with a spherical IOL implanted to give good uncorrected vision at a negligible pupil size. The effective refraction has been plotted against the diameter of the pupil with and without correction for the Stiles-Crawford effect. FIG. 7 illustrates the effect of pupil size on the refraction predicted for a normal eye of average dimension with a spherical IOL implant. As the pupil widens, the eye becomes myopic as a result of spherical aberration. The effect is compensated for by the Stiles-Crawford effect ('SC'). Two observations can be drawn from FIG. 7:

1) The effective refraction is dependent on the pupil size also within the normal range (less than 3-4 mm), and
2) The Stiles-Crawford effect compensates for the spherical aberration at larger pupil sizes.

Example 3

Determination of IOL Power Actually Implanted ('in situ')

The refractive outcome (spectacle correction) of 53 eyes with an IOL implant with good postoperative visual acuity (>20/40) was evaluated. The cases were selected to cover a large range of IOL powers but otherwise randomly chosen from the consecutive series of lens surgeries performed at the Cataract Clinic, University of Aarhus, Denmark. The IOL implanted was an IOL of spherical design (Alcon SA60AT Acrysof) with a labelled power ranging from +2.0 to +40.0 D.

IOL Data

The assumed physical characteristics of the IOL (thickness, refractive index, front and back curvature were obtained from the 'cutting chart' provided by Alcon). The example of the cutting chart is given in the table 2.

TABLE 2

'Cutting' chart provided from Alcon Laboratories showing the radii of the anterior and posterior surface of the IOL according to power.
SA60AT & SN60AT

| Diopter Range | Anterior Radii | Posterior Radii |
| --- | --- | --- |
| 6.0-9.5 D | 35-81 mm | 75.0 mm |
| 10.0-15.5 D | 22-52 mm | 37.7 mm |
| 16.0-25.0 D | 13.4-29.9 mm | 25.1 mm |
| 25.5-30.0 D | 12.6-16.9 mm | 17.48 mm |
| 31.0-40.0 D | 6.9-9.8 mm | 25.1 mm |

The refractive index is 1.5542 (Wavelength 550 nm) and the thickness is 0.8 mm for a normal power of about 23.0 D. (Data provided by Alcon Laboratories).

By ANSI definition, the power of an IOL can be calculated as the 'thick lens' paraxial power:

$$D_{12} = D_1 - \frac{T}{n} D_1 D_2$$

where $D_{12}$=total dioptric power of the lens, $D_1$=dioptric power of front surface, $D_2$=dioptric power of back surface, T=thickness of lens (in meters) and n=refractive index.

$D_1$ and $D_2$ can be found as:

$$D_1 = \frac{n - 1.336}{r_1} \text{ and } D_2 = \frac{1.336 - n}{r_2}$$

where $r_1$=radius of curvature of front surface (m), $r_2$=radius of curvature of back surface (with sign convention) and n=refractive index of the lens. In this way the exact curvatures of the IOL can be found from the labelled power according to the scheme in table 2.

Clinical Data

The anterior corneal radius was measured in two meridians by an auto-kerato-refractometer (ARK700; Nidek, Hiroishi, Japan) and the two readings averaged, which is the common procedure when dealing with spherical equivalents. The axial length was measured using optical partial coherence (Zeiss IOLMaster (Zeiss Meditec, Jena, Germany)). The postoperative anterior chamber depth ($ACD_{post}$) was measured by ultrasound (Tomey AL-2000, Tomey Corp., Nagoya, Japan) assuming a velocity of ultrasound of 1532 m/s for the distance from the corneal surface to the anterior surface of the IOL. A summary of the clinical data is shown in table 3.

TABLE 3

Clinical data of 53 cases with a known IOL implant. The postoperative position of the IOL was measured as the anterior chamber depth ($ACD_{post}$).

| | Data | | | | |
| --- | --- | --- | --- | --- | --- |
| | Age (years) | Preop Refraction (D) | Axial Length (mm) | IOL power (D) | Postoperative ACD (mm) |
| Mean (±SD) | 62.3 (±13.7) | −2.67 (±7.97) | 24.15 (±3.15) | 20.13 (±9.16) | 4.68 (±0.46) |
| Range | 30-88 | −18.63-+9.50 | 17.91-32.12 | 2.00-40.00 | 3.58-5.78 |

Mean values (±SD, standard deviation) and range are shown.

To study the validity of the postoperative anterior chamber depth, this variable was also measured by Pentacam (Oculus Optikgeraete, Wetzlar, Germany) in a subgroup of 10 cases. The measurement was performed as the average value of at least two perpendicularly oriented Scheimpflug scans, where the location of the anterior surface of the IOL could be identified. A calliper was used to estimate the distance from the corneal surface to the anterior surface of the IOL. FIG. 8 shows the position of the IOL determined from a Scheimpflug image of the anterior segment of a newly operated patient. The distance from the anterior surface of the cornea (81) to the anterior surface of the IOL (82) has been measured to be 5175 μm using a calliper.

The measurements provided by Scheimpflug imaging showed a highly statistically significant correlation with the ultrasound measurements (FIG. 9) with no significant difference between them (table 4).

TABLE 4

The postoperative ACD measured in 10 cases by ultrasound as well as by Scheimpflug (Pentacam) photography, respectively.

| Postoperative ACD (mm) | Ultrasound | Pentacam | Difference |
|---|---|---|---|
| Mean | 4.60 | 4.64 | 0.04 |
| (±SD) | (±0.21) | (±0.22) | (±0.05) |
| Range | 4.30-4.97 | 4.33-5.11 | −0.02-+0.14 |

The difference between the two measurements was not statistically significant ($p > 0.05$).

FIG. 9 illustrates the postoperative ACD measured in 10 cases by ultrasound as well as by Scheimpflug (Pentacam) photography, respectively. The correlation coefficient was 0.96 ($p<0.001$). The difference between the two measurements was not statistically significant ($p>0.05$).

The calculation of IOL power in situ was performed using 'thick lens' calculations as well as exact ray tracing techniques. The 'thick lens' calculations followed the principles described by Olsen (Olsen, 1987, Olsen, 2004) back-calculating for the IOL power to produce the actual refractive result. For the spherical IOL optic the average dependence between refractive index, thickness, anterior and posterior axial curvatures and power of the IOL optic was based on the cutting charts provided by the manufacturer.

The ray tracing calculations were performed by computer iteration to vary the anterior curvature of the IOL (within the segments shown in table II) until the best focus was found to coincide with the retina. An average pupil size of 3 mm (aperture projected to corneal surface) was assumed for all cases.

Results

Using 'thick lens' calculations a very high correlation was found between the calculated and observed power of the IOL, irrespective of IOL design (r=0.996, $p<0.0001$). The mean error (±SD) between the labelled and the calculated power of the spherical IOLs (calculated minus observed value) was −0.18 D (±0.88 D). The corresponding 95% confidence limits for the mean value were from −0.43 D to +0.06 D which were not significantly different from zero. For the aspherical IOLs the mean error was −1.25 D (±0.86 D). The corresponding 95% confidence limits were from −1.88 D to −0.61 D which were significantly different from zero ($p<0.05$). For the spherical IOLs a significant bias ($p<0.05$) was found between the prediction error and the IOL power. Using linear regression analysis a regression coefficient of 0.50 was found ($p<0.001$)

On the contrary when using exact ray tracing: no significant bias was found between the prediction error and the IOL power ($p>0.05$). Using ray tracing the mean error (±SD) between the labelled and the calculated power of the spherical IOLs was found to be −0.14 D (±0.66 D). The corresponding 95% confidence limits for the mean value were from −0.63 D to +0.36 D which were not significantly different from zero. The variance of the error with the ray tracing technique was lower than that of the 'thick lens' calculation, however not significant at the 0.05 level (F-test showed p=0.056).

FIG. 10 shows the IOL power calculated by ray tracing plotted against the labelled power in 53 eyes. A highly significant correlation was found between the calculated and the labelled power: r>0.99, $p<0.00001$. FIG. 11 shows the difference between the calculated and the labelled IOL power. FIG. 12 shows the difference between the calculated and the labelled IOL power plotted against the axial length of the eye. There was no significant correlation ($p>0.05$). The mean error (±SD) was found to be −0.14 D (±0.66 D), not statistically significant from zero ($p>0.05$). The corresponding 95% confidence limits for the mean value were from −0.63 D to +0.36 D, not significantly different from zero. There was no significant bias with the axial length.

Discussion

The errors associated with the estimation of the power of an IOL in situ are similar to the errors associated with the calculation of the IOL power before surgery. Traditionally, these errors have been divided into axial length errors, keratometry errors, and errors in the prediction of the postoperative ACD of the pseudophakic eye (Olsen, 1992). After surgery, however, the ACD is not to be predicted anymore—it only has to be measured. Recognizing the high precision of optical coherence interferometry for the measurement of axial length of the pseudophakic eye (Olsen and Thorwest, 2005a), may therefore provide a better condition for the biometric determination of the power of the IOL in situ as compared to using ultrasound for the measurement of axial length.

The present method is depending on an accurate ACD measurement of the pseudophakic eye. It may be argued that ultrasound measurements are not reliable due to a number of errors, i.e. possible indentation of the cornea, beam width, beam focusing and calibration problems. However, the high correlation between the ultrasound and the optical measurements illustrated previously shows that the ultrasound method may give a valid estimation of the ACD variation, regardless of possible off-set problems.

This example has shown that it is possible to estimate the power of an IOL in situ to an accuracy of 0.88 D and 0.66 D (SD) using 'thick lens' and ray tracing techniques, respectively. If one were to correct for off-set errors (by the application of average correction terms) this error corresponds to an accuracy within ±1 D in 74.4% of the cases using 'thick lens' calculation and 87.0% using ray tracing, respectively. As an error in the IOL power of 1.5 D corresponds to about 1.0 D in refractive power this means that a wrong IOL power causing more than a 1.0 D refractive error will have a 91.2% probability of being diagnosed with the 'thick lens' method and a 97.7% probability of being diagnosed with the ray tracing method.

To be noted here is the improved performance of the ray tracing method which was able to eliminate the bias with IOL power and to narrow the scatter. This result was attributed to the spherical aberration of the spherical IOL being more pronounced the higher the power. Also to be considered is the fact that the present results were obtained using an average pupil size. It is thus possible that a more accurate result may be found when the pupil diameter is measured and used in the calculations in the individual case.

These results were seen with spherical IOLs which have no correction for spherical aberration. In case of aspherical IOLs the 'thick lens' calculation resulted in an underestimation of the labelled IOL power. This is due to the fact that the labelled power by definition is the paraxial power and not the effective power. Due to the aspherical design the effective power of an aspherical IOL is less than that of a spherical IOL requiring a higher labelled power to obtain the same refractive result. However, presently the exact physical profiles of the various aspherical designs are regarded as proprietary information and not readily available. Thus, surgeons are left with the empirical observations of differences in A-constants from which the differences in effective power can be deduced.

To be able to calculate the power of the IOL in situ it would be helpful if the physical dimensions of the IOL in question are known. The time may call for a renewed policy of the IOL manufacturers to document these data as they are necessary in the detailed evaluation of the pseudophakic patient.

It is possible to determine the radius of curvature of an IOL in situ using the Purkinje-Sanson III and IV images. The method is cumbersome, however, and especially the flat curvature of the back surface may be difficult to measure using current equipment. Another possibility is to back-solve for the IOL power from the actual biometric measurements of the pseudophakic eye.

The accuracy of biometric determination cannot compete with measurements of the curvatures of the IOL, but this technique requires special equipment. The reason why the biometric determination today may be a valuable supplement to verifying the power in situ is the much higher accuracy of modern axial length measurements, especially with the Zeiss IOLMaster© or with the Haag-Streit Lenstar© instrument.

Because of the increased accuracy of optical biometry as compared to ultrasound, the prediction of the postoperative ACD has replaced the axial length measurement as the largest source of error in the prediction of the refractive outcome of IOL implantation.

Therefore it is logical to measure the ACD and to use this 'true' value in the formula thereby minimizing the error from this source, provided the formula is capable of utilizing this parameter. This is the case with 'thick lens' formulas like the Olsen formula, but cannot be made with formulas using the 'effective lens plane (ELP)' which refers to a virtual distance in the eye.

Example 4

Measurement of the Postoperative Anterior Chamber Depth

The patients and the clinical methods were the same as used in example 3, but in this context the calculations were reversed to estimate the effective $ACD_{post}$ from the measured data and the labelled power of the IOL. The calculated $ACD_{post}$ was then compared to the ACD measured by ultrasound. FIG. 13 shows the calculated ACD plotted against the measured ACD (ACD obs) in 53 eyes with a known IOL implant. A highly significant correlation was found between the calculated and the labelled ACD: $r=0.55$, $p<0.01$. FIG. 14 shows the difference between the calculated and the measured ACD in 53 eyes with a known IOL implant. The mean error ($\pm$SD) between the measured and the calculated ACD (observed-calculated) was found to be $-0.04$ mm ($\pm 0.44$ mm), which was not significantly different from zero: $t=-0.69$, $p>0.05$.

Examples 3 and 4 demonstrate that the model used in the present approach represents a realistic model of the eye with an IOL implant.

Example 5

Large Scale Statistical Analysis

A total of 4479 cataract cases were included in the study, comprising a consecutive series of routine cases with recorded refractive result after phacoemulsification with the implantation of a foldable intraocular lens of known optical design. The lenses were Alcon hydrophobic acrylic MA60BM or MA60AC Acrysof. These lenses were of similar design and the cutting charts were provided by the manufacturer so that exact physical data of the lenses could be used in the calculations.

Exclusion criteria were eyes with IOL implantation outside the capsular bag, dislocated lenses, previous anterior or posterior segment surgery, negative IOL power and preoperative or postoperative astigmatism larger than 4 D. For the present study, only cases with a postoperative best corrected visual acuity of 20/50 or more were included. The postoperative follow-up time was set from 1 week to 180 days.

Before surgery all patients were subjected to a routine preoperative evaluation including measurement of subjective refraction, corneal radius by keratometry, corneal diameter ('white-to-white') and axial length by optical biometry (Zeiss IOL Master©). The reading of the Zeiss IOLMaster was converted into optical path length as described previously. The preoperative anterior chamber depth and the lens thickness were measured by A-scan ultrasound (Tomey AL-2000) assuming a velocity of 1532 m/s and 1641 m/s, respectively (Jansson and Kock, 1962). The corneal radius was measured in two meridians by an auto-kerato-refractometer (Nidek ARK700) and the two readings averaged. The biometric and keratometric equipment were regularly calibrated to give the correct readings on a phantom eye. The clinical data are shown in table 5.

TABLE 5

Clinical data of 4479 IOL implantations

| Clinical Data | Age (y) | Preop Refraction (D) | Cornal radius (mm) | Corneal diameter (mm) | Preoperative ACD (mm) | Lens thickness (mm) | Axial Length (mm) |
| --- | --- | --- | --- | --- | --- | --- | --- |
| Mean | 73.7 | −0.30 | 7.75 | 12.1 | 3.15 | 4.70 | 23.50 |
| (±SD) | (±10.5) | (±3.38) | (±0.28) | (±0.44) | (±0.49) | (±0.48) | (±1.32) |
| Range | 20-98 | −26-+10.75 | 6.87-10.00 | 9.49-14.57 | 1.98-5.68 | 3.4-5.99 | 17.91-32.12 |

Based on the recorded postoperative refraction and the power of the implanted IOL the effective postoperative anterior chamber depth (defined as the distance from the corneal surface to the anterior surface of the lens) was calculated in each case by computer iteration solving for the $ACD_{post}$ that predicted the actual postoperative refraction within $\pm 0.01$ D (spherical equivalent) using the ray tracing technique. An average pupil diameter of 3 mm (normal value for this age group) was assumed for all cases.

The effective $ACD_{post}$ thus calculated was studied by multiple (distributional) linear regression for covariance with a number of preoperatively defined variables including the age of patient, the preoperative refraction, the corneal radius by keratometry, the height of the corneal segment, the axial length, the anterior chamber depth and the lens thickness.

Regression Analysis

A mean calculated postoperative ACD of 4.77 mm (±0.52, SD) was found. The postoperative ACD was found to be highly significantly (p<0.00001) correlated with 5 preoperative variables in combination: the axial length, the preoperative ACD, the corneal radius, the lens thickness and the age in decreasing order, respectively (table 6)

TABLE 6

Multiple regression analysis of the postoperative ACD in 4479 IOL implant cases. The overall regression coefficient 'r' was 0.44 (p < 0.000001).

|  | Coefficients | SEM | t-stat | P-value | Lower 95% CI | Upper 95% CI |
|---|---|---|---|---|---|---|
| Axial length | 0.1059 | 0.0068 | 16.30 | <0.00001 | 0.094 | 0.120 |
| Preoperative ACD | 0.3080 | 0.0203 | 15.53 | <0.00001 | 0.267 | 0.344 |
| Corneal radius | −0.4320 | 0.0294 | −15.30 | <0.00001 | −0.489 | −0.380 |
| Lens thicknes | 0.1918 | 0.0282 | 9.89 | <0.00001 | 0.155 | 0.225 |
| Age | −0.0035 | 0.0008 | −4.51 | <0.00001 | −0.004 | −0.002 |

SEM denotes standard deviation of the mean coefficient,
CI denotes confidence interval of the regression coefficients.

Based on the regression coefficients of table 6, the following regression equation predicting the postoperative ACD could be established:

$$ACD_{post,\,exp} = ACD_{post,\,mean} + 0.1059*(Ax - Ax_{mean}) + 0.3080*(ACD_{pre} - ACD_{pre,\,mean}) - 0.4320*(CR - CR_{mean}) + 0.1918*(LT - LT_{mean}) - 0.0035*(Age - Age_{mean})$$

with the following definitions:

$ACD_{post,\,exp}$=expected postoperative ACD of the given patient $ACD_{post,\,mean}$=mean postoperative ACD of the IOL $Ax_{mean}$=mean axial length Ax=axial length of patient in mm $ACD_{pre,\,mean}$=mean preoperative anterior chamber depth $ACD_{pre}$=preoperative anterior chamber depth of patient in mm $CR_{mean}$=mean average corneal radius in mm CR=average corneal radius of patient in mm $LT_{mean}$=mean lens thickness LT=lens thickness of patient in mm $Age_{mean}$=mean age of patients Age=age of patient.

Substituting for the mean values in the system, equation (10) reduces to:

$$ACD_{post,\,exp} = 4.01 + 0.1059*Ax + 0.308*ACD_{pre} - 0.432*CR + 0.1918*LT - 0.0035*Age$$

The off-set constant of 4.01 is the sum of $ACD_{post,\,mean}$ and the mean values times the coefficients of the regression variables.

To study the efficiency of this statistical fomula, all IOL power calculations were repeated using the expression for $ACD_{post,\,exp}$. The expected refraction was found by means of ray tracing by solving for the curvature of the spectacle corrective glass giving the best focus at the retina as shown in the case example of table 7. The error was defined as the observed refraction (spherical equivalent) minus the observed refraction (spherical equivalent). The calculations were performed without the use of any corrective terms, or other adjustment factors to account for hidden off-set factors in the system.

TABLE 7

Case example of analysis for expected spectacle correction.

| Surface | Name | x-Pos (mm) | Radius (mm) | Conic | index |
|---|---|---|---|---|---|
| 0 | Object | −30 | 10000 | 0 | 1 |
| 1 | Rx Front | −12.5 | 2000 | 0 | 1.49 |
| 2 | Rx Back | −12 | 931.49 | 0 | 1 |
| 3 | Cornea Front | 0 | 7.58 | −0.01 | 1.38 |
| 4 | Cornea Back | 0.5 | 6.36 | −0.48 | 1.34 |

TABLE 7-continued

Case example of analysis for expected spectacle correction.

| Surface | Name | x-Pos (mm) | Radius (mm) | Conic | index |
|---|---|---|---|---|---|
| 5 | Lens Front | 5.01 | 26.1 | 0 | 1.55 |
| 6 | Lens Back | 5.81 | −25.1 | 0 | 1.34 |
| 7 | Retina | 24.61 | −16 | 0 | 0 |

The radius of the back surface of the spectacles ('Rx Back') was varied by iteration until the best focus coincided with the retinal position (the axial length). The 'best focus' was defined as the plane with the minimal RMS. FIG. 15 shows the point spread function of the case shown in this table, for which the minimum blur (RMS) was found. The RMS was in this case found to be 0.0289. The radii of the anterior IOL curvature ('Lens Front') and the posterior IOL curvature ('Lens Back') were taken from the cutting chart of the manufacturer giving the implanted power of the IOL, in this case a +17.0 D IOL.

Results

FIG. 16 shows the distribution of the prediction error, defined as the difference (O−E) between the observed and the expected refraction in 4479 IOL implant cases. The mean error (±SD) of the predictions was found to be +0.01 D (±0.65), which was not significantly different from zero. The number of errors within ±0.5 D and ±1.0 D was 59.5% and 88.1%, respectively. The error ranged from −2.55 D to +2.47 D.

FIG. 17 shows the prediction error plotted against the axial length of 4479 eyes. When plotted against the axial length the error was found to be independent of the axial length with the exception of the very short eyes where a mean error of −1.13 D (±0.73) was found. This group included only 8 eyes with an axial length from 17.91 to 19.88 mm, however. For the remaining eyes, no significant bias with the axial length was found.

Another way of showing the error is to take the absolute value of the error. FIG. 18 the mean absolute error, defined as the absolute value of the difference (O−E) between the observed and the expected refraction in 4479 IOL implant cases. It is seen that the overall error was depending on the axial length with the lowest error in the long eyes and the highest error in the short eyes (<21 mm). For the remaining eyes the mean error was about 0.5 D.

Example 6

Improving the Empirical Procedures

Because the present approach requires no other empirical constant than the average postoperative ACD, this example will be based on direct measurements of the postoperative ACD in a representative number of patients and to use this value directly to adjust the average IOL position. The efficiency of this method as apposed to the older method will be demonstrated.

The statistical error (±SD) associated with the measurement of $ACD_{post}$ is typically around 0.46 mm D (cf. table 3—however the value of this table must be assumed to be a maximum value due to the inclusion of unusually long and short eyes). Assuming that 0.1 mm change of $ACD_{post}$ is the equivalent of a 0.19 D change in the IOL power (assuming average eye data) this means, that the ACD error of 0.46 mm is the equivalent of about 0.87 D IOL power (about 38% reduction compared to old method using the refractive outcome).

It is not necessary to measure the $ACD_{post}$ directly, however. As demonstrated in the previous section: if the clinician has data on the corneal power, the axial length and data for the physical dimensions of the IOL actually implanted, including its power, it is possible to calculate the $ACD_{post}$ in these cases by ray tracing according to the present model. For the present series of 4479 cases the SD of the calculated ACD of 0.52 mm was found (se example 5).

Again assuming that 0.1 mm change of $ACD_{post}$ is the equivalent of a 0.19 D change in the IOL power (assuming average eye data) this means that the calculated $ACD_{post}$ error of 0.52 mm is the equivalent of about 0.98 D IOL power (about 30% reduction compared to old method using the refractive outcome).

Example 7

Improving the Empirical Procedures

Based on the established regression equation 10 it is possible to deduce the average ACD as a function of the measured values according to:

$$ACD_{post, mean} = ACD_{post} - 0.1059*(Ax - Ax_{mean}) - 0.3080*(ACD_{pre} - ACD_{pre, mean}) + 0.4320*(CR - CR_{mean}) - 0.1918*(LT - LT_{mean}) + 0.0035*(Age - Age_{mean})$$

where
$ACD_{post}$ = measured postoperative ACD of the patient
$ACD_{post, mean}$ = mean postoperative ACD of the IOL
$Ax_{mean}$ = mean axial length
Ax = axial length of patient in mm
$ACD_{pre, mean}$ = mean preoperative anterior chamber depth
$ACD_{pre}$ = preoperative anterior chamber depth of patient in mm
$CR_{mean}$ = mean average corneal radius in mm
CR = average corneal radius of patient in mm
$LT_{mean}$ = mean lens thickness
LT = lens thickness of patient in mm
$Age_{mean}$ = mean age of patients
Age = age of patient.

The advantage of this formula is that the actual measurements are 'normalized' toward the mean value according to the individual readings of the axial length, the preoperative ACD, the corneal curvature, the lens thickness and the age. As a consequence, the variance of the estimated mean $ACD_{post}$ is reduced.

Based on the cases shown in table 3, the measured ACD was converted into a 'normalized' value ('ACD normalized'—method 2) in each case and the overall mean value (±SD) was calculated as shown in table 8. For comparison, the average IOL power according to the old refractive method and the non-manipulated ACD method ('ACD measured'—method 1) are also shown.

TABLE 8

Estimation of empirical IOL constants (A-constant according to SRK formula and ACD constant according to Olsen formula) in 53 cases, in which the postoperative position of the IOL was measured as the anterior chamber depth ($ACD_{post}$).

| | Data | | | |
|---|---|---|---|---|
| | IOL implant power (D) | A-constant (D) | ACD measured (mm) | ACD normalized (mm) |
| Mean | +20.13 | 120.1 | 4.68 | 4.68 |
| (±SD) | (±9.16) | (±2.47) | (±3.58) | (±0.27) |
| Range | +2.00-+40.00 | 114.8-127.7 | 3.58-5.78 | 4.05-5.51 |

Mean values (±SD, standard deviation) and range are shown.

The standard deviation of 2.47 for the A-constant is greater than the aforementioned value of 1.4 D from (Olsen, 2007) due to the inclusion of a high number of long and short eyes.

Again assuming that 0.1 mm change of $ACD_{post}$ is the equivalent of a 0.19 D change in the IOL power, it is possible to calculate the corresponding 95% confidence limits for the error associated with the necessary IOL constant (the confidence limits are proportional to the standard deviation of the estimate) for the three methods. This is shown in FIG. 19, where confidence limits for the estimation of IOL constants (in SRK A—constant IOL power equivalent units) according to three methods used on the content of table 3+8. The refractive method (old method) is seen to require about 100 cases for the confidence limits to be within ±1.0 D (squared points). The measured ACD method from example 6 ('ACDm'—method 1, triangle points) is seen to be within the equivalent value of ±1.0 D for less than 20 cases. The most effective method was found to be the normalized ACD method from example 7 ('ACDo'—method 2, round points), which was found to be twice as effective as the 'ACDm' method reaching confidence limits within ±0.20 D for 100 observations.

The old refractive method is seen to require about 100 cases for the confidence limits to be within ±1.0 D. The measured ACD method from example 6 is seen to be within the equivalent value of ±1.0 D for less than 20 cases. The most effective method was found to be the normalized ACD method from example 7, which was twice as effective as the measured ACD method reaching confidence limits within ±0.20 D for 100 observations.

Further Details of the Invention

The invention will now be described in more detail by means of the following sequentially numbered items:
1. A method for determining the postoperative power of an intraocular lens (IOL) in an eye of a patient, said IOL having known power and geometry, said method comprising the steps of:
   a) obtaining, measuring and/or calculating at least one of the following parameters of the pseudophakic eye of the patient: the axial length, the postoperative anterior chamber depth, corneal radius and the diameter of the pupil, and
   b) ray tracing analysis of an optical model of the pseudophakic eye at least partly based on the parameters obtained in step a),
   whereby the IOL power in situ is calculated.

2. A method for preoperatively predicting the optical properties of a pseudophakic eye of a patient with an IOL of known power and geometry, said method comprising the steps of:
   a) statistical analysis of clinical data from a plurality of eye operated patients,
   b) calculating, obtaining and/or measuring at least one of the following parameters of the phakic eye of the patient: the axial length, the preoperative anterior chamber depth, the corneal radius, the diameter of the pupil and the lens thickness,
   c) calculating the expected postoperative position of the IOL in the pseudophakic eye of the patient based on the statistical analysis from step a) and the parameters of the phakic eye of the patient provided in step b), and
   d) ray tracing analysis of a model of the pseudophakic eye, said ray tracing analysis at least partly based on the expected postoperative position of the IOL obtained in step d), whereby the IOL power in situ is calculated, thereby predicting the optical properties of the pseudophakic eye of the patient prior to surgery.
3. A method according to any of the preceding items, wherein the postoperative anterior chamber depth of the eye of a patient is calculated by means of ray tracing analysis of a model of the eye, partly based on the measured postoperative refractive properties of said eye.
4. A method according to any of the preceding items, wherein the axial length of an eye is measured by means of optical partial coherence interferometry, preferably by means of a Zeiss IOLMaster or a Lenstar LS 900 instrument.
5. A method according to item 4, wherein the axial length output from a Zeiss IOLMaster or a Lenstar LS 900 instrument is corrected to provide the true axial length of an eye.
6. A method according to item 5, wherein the true axial length of an eye is expressed as $AL_{True}=(AL_{Zeiss}*K_1+K_2)*K_3/K_4$ where $AL_{Zeiss}$ is the axial length output from a Zeiss IOLMaster or Lenstar LS 900 instrument and $K_1, K_2, K_3$ and $K_4$ are numerical constants.
7. A method according to item 6, wherein $K_1=0.9571$, $K_2=1.3033$, $K_3=1.3549$ and $K_4=1.3616$ where $K_4$ is the refractive index of an eye.
8. A method according to any of the preceding items, wherein an average pupil size of 3 mm is assumed in the ray tracing model.
9. A method according to any of the preceding items, wherein the radius of the anterior surface of the cornea is measured by means of keratometry, preferably by means of an autokerato-refractometer, and/or by means of corneal topography and wherein the radius of the posterior surface of the cornea is assumed to be a fixed ratio of the radius of the anterior surface of the cornea.
10. A method according to item 9, wherein the radius of the posterior surface of the cornea is assumed to 0.84 times the radius of the anterior surface of the cornea.
11. A method according to any of the preceding items, wherein the aspherical coefficient of the posterior corneal surface is assumed to be linearly dependent on the aspherical coefficient of the anterior corneal surface and wherein the aspherical coefficients of the posterior and the anterior corneal surfaces are assumed to be depending on the age of the patient.
12. A method according to any of the preceding items, wherein the aspherical coefficient of the anterior corneal surface is assumed to be 0.76 plus 0.003 times the age of the patient and the aspherical coefficient of the posterior corneal surface is assumed to be 0.76 plus 0.325 times the aspherical coefficient of the anterior corneal surface minus 0.0072 times the age of the patient.
13. A method according to any of the preceding items, wherein the preoperative anterior chamber depth ($ACD_{pre}$) and/or the postoperative anterior chamber depth ($ACD_{post, obs}$) are measured by means of ultrasound and/or by means of optical techniques, such as partial coherence interferometry or Scheimpflug imaging.
14. A method according to item 13, wherein an ultrasound velocity of 1532 m/s for the distance from the corneal surface to the anterior surface of the IOL is assumed in the ultrasound measurement of the postoperative anterior chamber depth.
15. A method according to item 13, wherein a Pentacam, such as an Oculus Optikgeraete instrument, is used for the Scheimpflug imaging and wherein the Scheimpflug imaging measurement is performed as the averaged value of at least two perpendicular oriented Scheimpflug scans where the location of the anterior surface of the IOL can be identified, and wherein a calliper is used to estimate the distance from the corneal surface to the anterior surface.
16. A method according to any of the preceding items, wherein the known power and geometry of the IOL is provided by the manufacturer's data for the refractive index and the thickness and the curvatures of the front and back surfaces of the IOL.
17. A method according to any of the preceding items, wherein the curvatures of the anterior and posterior surfaces of the IOL are calculated from the manufacturer's data for labelled power, anterior radii and posterior radii of the IOL.
18. A method according to any of the preceding items, wherein the model of the eye in the ray tracing analysis is provided with a plurality of surfaces, such as at least one of the following surfaces: the anterior corneal surface, the posterior corneal surface, the IOL anterior surface, the IOL posterior surface and the retina.
19. A method according to any of the preceding items, wherein the age of the patient is included in obtaining the expected postoperative anterior chamber depth.
20. A method according to any of the preceding items, wherein the age of each operated patient is obtained and/or at least one of the following parameters have been calculated, obtained and/or measured on each of the operated eyes of the eye operated patients: preoperative refractive properties, postoperative refractive properties, axial length, preoperative anterior chamber depth, postoperative anterior chamber depth, average corneal radius, diameter of pupil and lens thickness.
21. A method according to any of the preceding items, wherein the statistical analysis on the plurality of eye operated patients comprises the step of calculating the mean value of at least one of the following parameters: postoperative anterior chamber depth, axial length, preoperative anterior chamber depth, lens thickness, corneal radius, and the age of the patients.
22. A method according to any of the preceding items, wherein multiple regression analysis is applied to the data of the plurality of eye operated patients, whereby the expected postoperative position of the IOL can be expressed as a function of at least one of the following parameters: mean postoperative chamber depth ($ACD_{post, mean}$), preoperative anterior chamber depth ($ACD_{pre}$), mean anterior chamber depth ($ACD_{pre, mean}$), axial length (Ax), mean axial length ($Ax_{mean}$), corneal radius (CR), mean corneal radius ($CR_{mean}$), lens thickness (LT), mean lens thickness ($LT_{mean}$), age (Age) and mean age ($Age_{mean}$).

23. A method according to any of the preceding items, whereby the expected postoperative position of the IOL is determined, preferably by means of calculating the expected postoperative anterior chamber depth ($ACD_{post, exp}$).

24. A method according to item 23, wherein the expected postoperative anterior chamber depth ($ACD_{post, exp}$) is expressed as:

$$ACD_{post, exp}=ACD_{post, mean}+C_1*(Ax-Ax_{mean})+C_2*(ACD_{pre}-ACD_{pre, mean})+C_3*(CR-CR_{mean})+C_4*(LT-LT_{mean})+C_5*(Age-Age_{mean}),$$

where $C_1$, $C_2$, $C_3$, $C_4$ and $C_5$ are numerical constants provided by the multiple regression analysis.

25. A method according to any of the preceding items, wherein the mean postoperative chamber depth ($ACD_{post, mean}$) is continuously adjusted to reflect any changes in IOL design and/or surgical techniques.

26. A method according to item 25, wherein the mean postoperative chamber depth ($ACD_{post, mean}$) is adjusted according to the following formula:

$$ACD_{post, mean}=ACD_{post}-C_1*(Ax-Ax_{mean})-C_2*(ACD_{pre}-ACD_{pre, mean})-C_3*(CR-CR_{mean})-C_4*(LT-LT_{mean})-C_5*(Age-Age_{mean}),$$

where $C_1$, $C_2$, $C_3$, $C_4$ and $C_5$ are numerical constants provided by the multiple regression analysis.

27. A method according to any of items 24 to 26, wherein the numerical constants $C_1$, $C_2$, $C_3$, $C_4$ and $C_5$ have the following values: $C_1=0.1059$, $C_2=0.308$, $C_3=0.432$ $C_4=0.1918$ and $C_5=-0.0035$.

28. A method according to any of the preceding items, wherein the IOL power is corrected for spherical aberration, preferably by means of the Stiles Crawford effect $I=I_0\exp(-C*\gamma^2)$, where C is a numerical constant and $\gamma$ is the distance from the centre of the pupil.

29. A method according to any of the preceding items, wherein the optical properties of the eye is assessed by calculating at least one point spread function evaluated at the retina of the eye and/or at the point of best focus.

30. A method for prevention, treatment and/or amelioration of a disease and/or disorder which is either related to a lens of an eye of a patient and/or which may benefit from the treatment of said lens, said method comprising the steps of:
v) providing an IOL of known power and geometry,
vi) calculating and evaluating the optical properties if said IOL were to be inserted in said eye of said patient, said calculation based on the method according to item Fejl! Henvisningskilde ikke fundet.,
vii) repeating steps i) and ii) until satisfactory optical properties have been obtained for a specific IOL, and
viii) inserting said specific IOL in the eye of the patient.

31. The method according to item 29, wherein the diseases and/or disorders are selected from: presbyopia; cataract at all stages; opacities, brunescence or cloudiness of the lens; refractive errors; myopia; hyperopia, astigmatism.

32. A system for determining the postoperative power of an intraocular lens (IOL) in an eye of a patient, said IOL having known power and geometry, said system comprising:
d) means for obtaining, measuring and/or calculating at least one of the following parameters of the pseudophakic eye of the patient: the axial length, the postoperative anterior chamber depth, corneal radius and the diameter of the pupil,
e) means for performing a ray tracing analysis of an optical model of the pseudophakic eye at least partly based on the parameters obtained in step a), and
f) means for calculating the IOL power in situ at least partly based on the ray tracing analysis performed in step b).

33. A system for preoperatively predicting the optical properties of a pseudophakic eye of a patient with an IOL of known power and geometry, said system comprising:
f) means for providing statistical analysis of clinical data from a plurality of eye operated patients,
g) means for calculating, obtaining and/or measuring at least one of the following parameters of the phakic eye of the patient: the axial length, the preoperative anterior chamber depth, the corneal radius, the diameter of the pupil and the lens thickness,
h) means calculating the expected postoperative position of the IOL in the pseudophakic eye of the patient based on the statistical analysis from step a) and the parameters of the phakic eye of the patient provided in step b), and
i) means for performing ray tracing analysis of a model of the pseudophakic eye, and
j) means for calculating the IOL power in situ at least partly based on the ray tracing analysis performed in step d).

34. A system according to any of the items 32 to 33, wherein the postoperative anterior chamber depth of the eye of an operated patient is calculated by means of a ray tracing analysis of a model of the eye, at least partly based on the measured postoperative refractive properties of said eye.

35. A system according to any of the items 32 to 34, wherein the axial length of an eye is measured by means of optical partial coherence interferometry, preferably by means of a Zeiss IOLMaster or a Lenstar LS 900 instrument.

36. A system according to item 35, wherein the axial length output from a Zeiss IOLMaster or a Lenstar LS 900 instrument is corrected to provide the true axial length of an eye.

37. A system according to item 36, wherein the true axial length of an eye is expressed as $AL_{True}=(AL_{Zeiss}*K_1+K_2)*K_3/K_4$ where $AL_{Zeiss}$ is the axial length output from a Zeiss IOLMaster or a Lenstar LS 900 instrument and $K_1$, $K_2$, $K_3$ and $K_4$ are numerical constants.

38. A system according to item 37, wherein $K_1=0.9571$, $K_2=1.3033$, $K_3=1.3549$ and $K_4=1.3616$ where $K_4$ is the refractive index of an eye.

39. A system according to any of the items 32 to 38, wherein an average pupil size of 3 mm is assumed in the ray tracing model.

40. A system according to any of the items 32 to 39, wherein the radius of the anterior surface of the cornea is measured by means of keratometry, preferably by means of an autokeratorefractometer, and/or by means of corneal topography and wherein the radius of the posterior surface of the cornea is assumed to be a fixed ratio of the radius of the anterior surface of the cornea.

41. A system according to item 40, wherein the radius of the posterior surface of the cornea is assumed to 0.84 times the radius of the anterior surface of the cornea.

42. A system according to any of the items 32 to 41, wherein the aspherical coefficient of the posterior corneal surface is assumed to be linearly dependent on the aspherical coefficient of the anterior corneal surface and wherein the aspherical coefficients of the posterior and the anterior corneal surfaces are assumed to be depending on the age of the patient.

43. A system according to any of the items 32 to 42, wherein the aspherical coefficient of the anterior corneal surface is assumed to be 0.76 plus 0.003 times the age of the patient and the aspherical coefficient of the posterior corneal surface is assumed to be 0.76 plus 0.325 times the aspherical coefficient of the anterior corneal surface minus 0.0072 times the age of the patient.

44. A system according to any of the items 32 to 43, wherein the preoperative anterior chamber depth ($ACD_{pre}$) and/or the postoperative anterior chamber depth ($ACD_{post, obs}$) are measured by means of ultrasound and/or by means of optical techniques, such as partial coherence interferometry or Scheimpflug imaging.

45. A system according to any of the items 32 to 44, wherein an ultrasound velocity of 1532 m/s for the distance from the corneal surface to the anterior surface of the IOL is assumed in the ultrasound measurement of the postoperative anterior chamber depth.

46. A system according to any of the items 32 to 45, wherein a Pentacam, such as an Oculus Optikgeraete instrument, is used for the Scheimpflug imaging and wherein the Scheimpflug imaging measurement is performed as the averaged value of at least two perpendicular oriented Scheimpflug scans where the location of the anterior surface of the IOL can be identified, and wherein a calliper is used to estimate the distance from the corneal surface to the anterior surface.

47. A system according to any of the items 32 to 46, wherein the known power and geometry of the IOL is provided by the manufacturer's data for the refractive index and the thickness and the curvatures of the front and back surfaces of the IOL.

48. A system according to any of the items 32 to 47, wherein the exact curvatures of the anterior and posterior surfaces of the IOL are calculated from the manufacturer's data for labelled power, anterior radii and posterior radii of the IOL.

49. A system according to any of the items 32 to 48, wherein the model of the eye in the ray tracing analysis is provided with a plurality of surfaces, such as at least one of the following surfaces: the anterior corneal surface, the posterior corneal surface, the IOL anterior surface, the IOL posterior surface and the retina.

50. A system according to any of the items 32 to 49, wherein the age of the patient is included in obtaining the expected postoperative anterior chamber depth.

51. A system according to any of the items 32 to 50, wherein the age of each operated patient is obtained and/or at least one of the following parameters have been calculated, obtained and/or measured on each of the operated eyes of the eye operated patients: preoperative refractive properties, postoperative refractive properties, axial length, preoperative anterior chamber depth, postoperative anterior chamber depth, average corneal radius, diameter of pupil and lens thickness.

52. A system according to any of the items 32 to 51, wherein the statistical analysis on the plurality of eye operated patients comprises the step of calculating the mean value of at least one of the following parameters: postoperative anterior chamber depth, axial length, preoperative anterior chamber depth, lens thickness, corneal radius, and the age of the patients.

53. A system according to any of the items 32 to 52, wherein multiple regression analysis is applied to the data of the plurality of eye operated patients, whereby the expected postoperative position of the IOL can be expressed as a function of at least one of the following parameters: mean postoperative chamber depth ($ACD_{post, mean}$), preoperative anterior chamber depth ($ACD_{pre}$), mean anterior chamber depth ($ACD_{pre, mean}$), axial length (Ax), mean axial length ($Ax_{mean}$), corneal radius (CR), mean corneal radius ($CR_{mean}$), lens thickness (LT), mean lens thickness ($LT_{mean}$), age (Age) and mean age ($Age_{mean}$).

54. A system according to any of the items 32 to 53, whereby the expected postoperative position of the IOL is determined, preferably by means of calculating the expected postoperative anterior chamber depth ($ACD_{post, exp}$).

55. A system according to item 54, wherein expected postoperative anterior chamber depth ($ACD_{post, exp}$) is expressed as:

$$ACD_{post, exp} = ACD_{post, mean} + C_1*(AX-AX_{mean}) + C_2*(ACD_{pre, mean}) + C_3*(CR-CR_{mean}) + C_4*(LT-LT_{mean}) + C_5*(Age-Age_{mean}),$$

where $C_1$, $C_2$, $C_3$, $C_4$ and $C_5$ are numerical constants provided by the multiple regression analysis.

56. A system according to any of the items 32 to 55, wherein the mean postoperative chamber depth ($ACD_{post, mean}$) is continuously adjusted to reflect any changes in IOL design and/or surgical techniques.

57. A system according to item 56, wherein the mean postoperative chamber depth ($ACD_{post, mean}$) is adjusted according to the following formula:

$$ACD_{post, mean} = ACD_{post} - C_1*(Ax-Ax_{mean}) - C_2*(ACD_{pre} - ACD_{pre, mean}) - C_3*(CR-CR_{mean}) - C_4*(LT-LT_{mean}) - C_5*(Age-Age_{mean}),$$

where $C_1$, $C_2$, $C_3$, $C_4$ and $C_5$ are numerical constants provided by the multiple regression analysis.

58. A system according to any of items 55 to 57, wherein the numerical constants $C_1$, $C_2$, $C_3$, $C_4$ and $C_5$ have the following values: $C_1=0.1059$, $C_2=0.308$, $C_3=-0.432$ $C_4=0.1918$ and $C_5=-0.0035$.

59. A system according to any of the items 32 to 57, wherein the IOL power is corrected for spherical aberration, preferably by means of the Stiles Crawford effect $I=I_0 exp(-C*\gamma^2)$, where C is a numerical constant and $\gamma$ is the distance from the centre of the pupil.

60. A system according to any of the items 32 to 59, wherein the optical properties of the eye is assessed by calculating at least one point spread function evaluated at the retina of the eye and/or at the point of best focus.

61. A system for prevention, treatment and/or amelioration of a disease and/or disorder which is either related to a lens of an eye of a patient and/or which may benefit from the treatment of said lens by means of IOL surgery, said system comprising:
v) means for providing an IOL of known power and geometry,
vi) means for calculating and evaluating the optical properties if said IOL were to be inserted in said eye of said patient, said calculation based on the method according to item 2,
vii) means for repeating steps i) and ii) until satisfactory optical properties have been obtained for a specific IOL, and
viii) means inserting said specific IOL in the eye of the patient.

62. The system according to item 61, wherein the diseases and/or disorders are selected from: presbyopia; cataract at all stages; opacities, brunescence or cloudiness of the lens; refractive errors; myopia; hyperopia, astigmatism.

63. A computer program product having a computer readable medium, said computer program product providing a system for determining the postoperative power of an intraocular lens (IOL) in an eye of a patient, said computer program product comprising means for carrying out all the steps of the method according to item 1.

64. A computer program product having a computer readable medium, said computer program product providing a system for preoperatively predicting the optical properties of a pseudophakic eye of a patient with an IOL of known power and geometry, said computer program product comprising means for carrying out all the steps of the method according to item 2.

REFERENCES

Baker T Y. Ray-tracing trough non-spherical surfaces. Proc Physical Soc (UK) 1943; (24): 361-364.

Binkhorst R D. The optical design of intraocular lens implants. Ophthalmic Surg 1975; (6): 17-31.

Binkhorst R D. Intraocular lens power calculation. Int Ophthalmol Clin 1979; (19): 237-252.

Colenbrander M C. Calculation of the power of an iris clip lens for distant vision. Br J Ophthalmol 1973; (57): 735-740.

Connors R, III, Boseman P, III, Olson R J. Accuracy and reproducibility of biometry using partial coherence interferometry. J Cataract Refract Surg 2002; (28): 235-238.

Drexler W, Findl O, Menapace R, Rainer G, Vass C, Hitzenberger C K, Fercher A F. Partial coherence interferometry: a novel approach to biometry in cataract surgery. Am J Ophthalmol 1998; (126): 524-534.

Dubbelman M, Sicam V A, van der Heijde G L. The shape of the anterior and posterior surface of the aging human cornea. Vision Res 2006; (46): 993-1001.

Dubbelman M, Weeber H A, van der Heijde R G, Volker-Dieben H J. Radius and asphericity of the posterior corneal surface determined by corrected Scheimpflug photography. Acta Ophthalmol Scand 2002; (80): 379-383.

Dunne M C, Royston J M, Barnes D A. Normal variations of the posterior corneal surface. Acta Ophthalmol (Copenh) 1992; (70): 255-261.

Findl O, Kriechbaum K, Sacu S, Kiss B, Polak K, Nepp J, Schild G, Rainer G, Maca S, Petternel V, Lackner B, Drexler W. Influence of operator experience on the performance of ultrasound biometry compared to optical biometry before cataract surgery. J Cataract Refract Surg 2003; (29): 1950-1955.

Fyodorov S N, Galin M A, Linksz A. Calculation of the optical power of intraocular lenses. Invest Ophthalmol 1975; (14): 625-628.

Gernet H. [Intraocular lens planning. Geometric-optical and Sanders-Retzlaff-Kraff I and II formulas]. Ophtalmologie 1990; (4): 96-101.

Gullstrand A. Die Dioptrik des Auges. In: Handbuch der physiologischen Optik. (Ed.Helmholz H). Hamburg: L Voss, 1909; 3: 41-375.

Gullstrand A. The dioptrics of the eye. In: Helmholtz's Treatise on Physiological Optics. (Ed.Southall JPC). Optical Society of America, 1924; 351-352.

Haigis W. Pseudophakic correction factors for optical biometry. Graefes Arch Clin Exp Ophthalmol 2001; (239): 589-598.

Haigis W. The Haigis formula. In: Intraocular lens power calculations. (Ed.Shammas HJ). Slack Inc, 2004; 5-57.

Haigis W, Lege B, Miller N, Schneider B. Comparison of immersion ultrasound biometry and partial coherence interferometry for intraocular lens calculation according to Haigis. Graefes Arch Clin Exp Ophthalmol 2000; (238): 765-773.

Hoffer K J. The Hoffer Q formula: a comparison of theoretic and regression formulas. J Cataract Refract Surg 1993b; (19): 700-712.

Hoffer K J. The Hoffer Q formula: a comparison of theoretic and regression formulas. J Cataract Refract Surg 1993a; (19): 700-712.

Hoffer K J. Clinical results using the Holladay 2 intraocular lens power formula. J Cataract Refract Surg 2000; (26): 1233-1237.

Holladay J T, Prager T C, Chandler T Y, Musgrove K H, Lewis J W, Ruiz R S. A three-part system for refining intraocular lens power calculations. J Cataract Refract Surg 1988; (14): 17-24.

Jansson F, Kock E. Determination of the velocity of ultrasound in the human lens and vitreous. Acta Ophthalmol (Copenh) 1962; (40): 420-433.

Kiss B, Findl O, Menapace R, Wirtitsch M, Petternel V, Drexler W, Rainer G, Georgopoulos M, Hitzenberger C K, Fercher A F. Refractive outcome of cataract surgery using partial coherence interferometry and ultrasound biometry: clinical feasibility study of a commercial prototype II. J Cataract Refract Surg 2002; (28): 230-234.

Olsen T. On the calculation of power from curvature of the cornea. Br J Ophthalmol 1986a; (70): 152-154.

Olsen T. Prediction of intraocular lens position after cataract extraction. J Cataract Refract Surg 1986b; (12): 376-379.

Olsen T. Theoretical approach to intraocular lens calculation using Gaussian optics. J Cataract Refract Surg 1987a; (13): 141-145.

Olsen T. Theoretical vs empirical prediction of aphakic refraction. Arch Ophthalmol 1987b; (105): 1042-1045.

Olsen T. Theoretical, computer-assisted prediction versus SRK prediction of postoperative refraction after intraocular lens implantation. J Cataract Refract Surg 1987c; (13): 146-150.

Olsen T. On the Stiles-Crawford effect and ocular imagery. Acta Ophthalmol (Copenh) 1993; (71): 85-88.

Olsen T. The Olsen formula. In: Intraocular lens calculations. (Ed.Shammas HJ). Thorofare, N.J.: Slack Inc, 2004; 27-40.

Olsen T. Prediction of the effective postoperative (intraocular lens) anterior chamber depth. J Cataract Refract Surg 2006b; (32): 419-424.

Olsen T. Prediction of the effective postoperative (intraocular lens) anterior chamber depth. J Cataract Refract Surg 2006a; (32): 419-424.

Olsen T. Calculation of intraocular lens power: a review. Acta Ophthalmol Scand 2007; (85): 472-485.

Olsen T, Corydon L. We don't need fudge factors in IOL power calculation. Eur J Implant Refract Surg 1993; (5): 51-54.

Olsen T, Corydon L, Gimbel H. Intraocular lens power calculation with an improved anterior chamber depth prediction algorithm. J Cataract Refract Surg 1995; (21): 313-319.

Olsen T, Gimbel H. Phacoemulsification, capsulorhexis, and intraocular lens power prediction accuracy. J Cataract Refract Surg 1993; (19): 695-699.

Olsen T, Olesen H, Thim K, Corydon L. Prediction of postoperative intraocular lens chamber depth. J Cataract Refract Surg 1990a; (16): 587-590.

Olsen T, Olesen H, Thim K, Corydon L. Prediction of pseudophakic anterior chamber depth with the newer IOL calculation formulas. J Cataract Refract Surg 1992; (18): 280-285.

Olsen T, Thim K, Corydon L. Theoretical versus SRK I and SRK II calculation of intraocular lens power. J Cataract Refract Surg 1990b; (16): 217-225.

Olsen T, Thim K, Corydon L. Accuracy of the newer generation intraocular lens power calculation formulas in long and short eyes. J Cataract Refract Surg 1991; (17): 187-193.

Olsen T, Thorwest M. Calibration of axial length measurements with the Zeiss IOLMaster. J Cataract Refract Surg 2005a; (31): 1345-1350.

Olsen T, Thorwest M. Calibration of axial length measurements with the Zeiss IOLMaster. J Cataract Refract Surg 2005b; (31): 1345-1350.

Packer M, Fine I H, Hoffman R S, Coffman P G, Brown L K. Immersion A-scan compared with partial coherence interferometry: outcomes analysis. J Cataract Refract Surg 2002; (28): 239-242.

Retzlaff J. A new intraocular lens calculation formula. J Am Intraocul Implant Soc 1980; (6): 148-152.

Retzlaff J A, Sanders D R, Kraff M C. Development of the SRK/T intraocular lens implant power calculation formula. J Cataract Refract Surg 1990; (16): 333-340.

Sanders D, Retzlaff J, Kraff M, Kratz R, Gills J, Levine R, Colvard M, Weisel J, Loyd T. Comparison of the accuracy of the Binkhorst, Colenbrander, and SRK implant power prediction formulas. J Am Intraocul Implant Soc 1981; (7): 337-340.

Sanders D R, Retzlaff J, Kraff M C. Comparison of the SRK II formula and other second generation formulas. J Cataract Refract Surg 1988; (14): 136-141.

Sanders D R, Retzlaff J A, Kraff M C, Gimbel H V, Raanan M G. Comparison of the SRK/T formula and other theoretical and regression formulas. J Cataract Refract Surg 1990; (16): 341-346.

Stiles W S, Crawford B H. The luminous efficiency of rays entering the eye pupil at different points. Proc Roy Soc (London) B 1933; (112): 428-450.

Vogel A, Dick H B, Krummenauer F. Reproducibility of optical biometry using partial coherence interferometry: intraobserver and interobserver reliability. J Cataract Refract Surg 2001; (27): 1961-1968.

The invention claimed is:

1. A method for determining the postoperative power of an intraocular lens (IOL) in an eye of a patient, said IOL having known power and geometry, said method comprising:
obtaining, measuring and/or calculating at least one of the following parameters of a pseudophakic eye of the patient: the axial length, the postoperative anterior chamber depth, the corneal radius and the diameter of the pupil,
performing a ray tracing analysis of an optical model of the pseudophakic eye, based on said parameters, and
calculating the IOL power in situ, based on said ray tracing analysis.

2. The method of claim 1, wherein the postoperative anterior chamber depth of the eye of an operated patient is calculated by means of a ray tracing analysis of a model of the pseudophakic eye, based on the measured postoperative refractive properties of said eye.

3. The method of claim 1, wherein the axial length of an eye is measured by means of optical partial coherence interferometry, preferably by means of a Zeiss IOLMaster or a Lenstar LS 900 instrument and wherein the axial length output from said instrument is corrected to provide the true axial length of an eye.

4. The method of claim 3, wherein the true axial length of an eye is expressed as $AL_{True}=(AL_{Zeiss}*K_1+K_2)*K_3/K_4$ where $AL_{Zeiss}$ is the axial length output from a Zeiss IOL-Master or a Lenstar LS 900 instrument and $K_1$, $K_2$, $K_3$ and $K_4$ are numerical constants.

5. The method of claim 1, wherein the radius of the anterior surface of the cornea is measured by means of keratometry, preferably by means of an autokeratorefractometer, and/or by means of corneal topography and wherein the radius of the posterior surface of the cornea is assumed to be a fixed ratio of the radius of the anterior surface of the cornea.

6. The method of claim 1, wherein the aspherical coefficient of the posterior corneal surface is assumed to be linearly dependent on the aspherical coefficient of the anterior corneal surface and wherein the aspherical coefficients of the posterior and the anterior corneal surfaces are assumed to be depending on the age of the patient.

7. The method of claim 1, wherein the preoperative anterior chamber depth ($ACD_{pre}$) and/or the postoperative anterior chamber depth ($ACD_{post, obs}$) are measured by means of ultrasound and/or by means of optical techniques, such as partial coherence interferometry or Scheimpflug imaging.

8. The method of claim 1, wherein the known power and geometry of the IOL is provided by the manufacturer's data for the refractive index and the thickness and the curvatures of the front and back surfaces of the IOL and wherein the exact curvatures of the anterior and posterior surfaces of the IOL are calculated from the manufacturer's data for labelled power, anterior radii and posterior radii of the IOL.

9. The method of claim 1, wherein the model of the eye in the ray tracing analysis is provided with a plurality of surfaces, such as one or more of the following surfaces: the anterior corneal surface, the posterior corneal surface, the IOL anterior surface, the IOL posterior surface and the retina.

10. The method of claim 1, wherein the mean postoperative chamber depth ($ACD_{post, mean}$) is continuously adjusted to reflect any changes in IOL design and/or surgical techniques.

11. The method of claim 1, wherein the IOL power is corrected for spherical aberration, preferably by means of the Stiles Crawford effect $I=I_0\exp(-C*\gamma^2)$, where C is a numerical constant and $\gamma$ is the distance from the centre of the pupil, and/or wherein the optical properties of the eye is assessed by calculating at least one point spread function evaluated at the retina of the eye and/or at the point of best focus.

12. A method for preoperatively predicting the optical properties of a pseudophakic eye of a patient with an IOL of known power and geometry, said method comprising:
performing statistical analysis of clinical data from a plurality of eye operated patients,
calculating, obtaining and/or measuring at least one of the following parameters of the phakic eye of the patient: the axial length, the preoperative anterior chamber depth, the corneal radius, the diameter of the pupil and the lens thickness,
calculating the expected postoperative position of the IOL in the pseudophakic eye of the patient based on said statistical analysis and the parameters of the phakic eye of the patient, and
performing ray tracing analysis of a model of the pseudophakic eye of the patient, and
calculating the IOL power in situ based on said ray tracing analysis.

13. The method of claim 12, wherein the age of each operated patient is obtained and/or at least one of the following parameters have been calculated, obtained and/or measured on each of the operated eyes of the eye operated patients: preoperative refractive properties, postoperative refractive properties, axial length, preoperative anterior chamber depth, postoperative anterior chamber depth, average corneal radius, diameter of pupil and lens thickness.

14. The method of claim 12, wherein the statistical analysis on the plurality of eye operated patients comprises the step of calculating the mean value of at least one of the following parameters:

postoperative anterior chamber depth, axial length, preoperative anterior chamber depth, lens thickness, corneal radius, and the age of the patients.

15. The method of claim 12, wherein multiple regression analysis is applied to the data of the plurality of eye operated patients, whereby the expected postoperative position of the IOL can be expressed as a function of one or more of the following parameters: mean postoperative chamber depth ($ACD_{post, mean}$) preoperative anterior chamber depth ($ACD_{pre}$), mean anterior chamber depth ($ACD_{pre, mean}$) axial length (Ax), mean axial length ($AX_{mean}$), corneal radius (CR), mean corneal radius ($CR_{mean}$), lens thickness (LT), mean lens thickness ($LT_{mean}$), age (Age) and mean age ($Age_{mean}$).

16. The method of claim 12, wherein the expected postoperative position of the IOL is determined, preferably by means of calculating the expected postoperative anterior chamber depth ($ACD_{post, exp}$) and wherein the $ACD_{post, exp}$ is expressed as:

$$ACD_{post, exp} = ACD_{post, mean} + C_1*(AX-AX_{mean}) + C_2*(ACD_{pre}-ACD_{pre, mean}) + C_3*(CR-CR_{mean}) + C_4*(LT-LT_{mean}) + C_5*(Age-Age_{mean}),$$

where $C_1, C_2, C_3, C_4$ and $C_5$ are numerical constants provided by the multiple regression analysis.

17. The method of claim 12, wherein the axial length of an eye is measured by means of optical partial coherence interferometry, preferably by means of a Zeiss IOLMaster or a Lenstar LS 900 instrument and wherein the axial length output from said instrument is corrected to provide the true axial length of an eye.

18. The method of claim 17, wherein the true axial length of an eye is expressed as $AL_{True} = (AL_{Zeiss}*K_1+K_2)*K_3/K_4$ where $AL_{Zeiss}$ is the axial length output from a Zeiss IOLMaster or a Lenstar LS 900 instrument and $K_1, K_2, K_3$ and $K_4$ are numerical constants.

19. The method of claim 12, wherein the radius of the anterior surface of the cornea is measured by means of keratometry, preferably by means of an autokeratorefractometer, and/or by means of corneal topography and wherein the radius of the posterior surface of the cornea is assumed to be a fixed ratio of the radius of the anterior surface of the cornea.

20. The method of claim 12, wherein the aspherical coefficient of the posterior corneal surface is assumed to be linearly dependent on the aspherical coefficient of the anterior corneal surface and wherein the aspherical coefficients of the posterior and the anterior corneal surfaces are assumed to be depending on the age of the patient.

21. The method of claim 12, wherein the preoperative anterior chamber depth ($ACD_{pre}$) and/or the postoperative anterior chamber depth ($ACD_{post, obs}$) are measured by means of ultrasound and/or by means of optical techniques, such as partial coherence interferometry or Scheimpflug imaging.

22. The method of claim 12, wherein the known power and geometry of the IOL is provided by the manufacturer's data for the refractive index and the thickness and the curvatures of the front and back surfaces of the IOL and wherein the exact curvatures of the anterior and posterior surfaces of the IOL are calculated from the manufacturer's data for labelled power, anterior radii and posterior radii of the IOL.

23. The method of claim 12, wherein the model of the eye in the ray tracing analysis is provided with a plurality of surfaces, such as one or more of the following surfaces: the anterior corneal surface, the posterior corneal surface, the IOL anterior surface, the IOL posterior surface and the retina.

24. The method of claim 12, wherein the mean postoperative chamber depth ($ACD_{post, mean}$) is continuously adjusted to reflect any changes in IOL design and/or surgical techniques.

25. The method of claim 12, wherein the IOL power is corrected for spherical aberration, preferably by means of the Stiles Crawford effect $I=I_0 exp(-C*\gamma^2)$, where C is a numerical constant and $\gamma$ is the distance from the centre of the pupil, and/or wherein the optical properties of the eye is assessed by calculating at least one point spread function evaluated at the retina of the eye and/or at the point of best focus.

26. A method for preoperatively predicting the optical properties of a pseudophakic eye of a patient with an IOL of known power and geometry, said method comprising the steps of:
a) performing statistical analysis of clinical data from a plurality of eye operated patients,
b) calculating, obtaining and/or measuring at least one of the following parameters of the phakic eye of the patient: the axial length, the preoperative anterior chamber depth, the corneal radius, the diameter of the pupil and the lens thickness,
c) calculating the expected postoperative position of the IOL in the pseudophakic eye of the patient based on the statistical analysis from step a) and the parameters of the phakic eye of the patient provided in step b), and
d) performing ray tracing analysis of a model of the pseudophakic eye, said ray tracing analysis based on the expected postoperative position of the IOL obtained in step d), whereby the IOL power in situ is calculated,
thereby predicting the optical properties of the pseudophakic eye of the patient prior to surgery.

27. A method for prevention, treatment and/or amelioration of a disease and/or disorder which is either related to a lens of an eye of a patient and/or which may benefit from the treatment of said lens by means of IOL surgery, said method comprising the steps of:
i) providing an IOL of known power and geometry,
ii) calculating and evaluating the refractive outcome if said IOL were to be inserted in said eye of said patient, said calculation based on the method according to claim 26,
iii) repeating steps i) and ii) until a satisfactory refractive outcome has been obtained for a specific IOL, and iv) inserting/implanting said specific IOL in the eye of the patient.

28. The method according to claim 27, wherein the diseases and/or disorders are selected from: presbyopia; cataract at all stages; opacities, brunescence or cloudiness of the lens; refractive errors; myopia; hyperopia, astigmatism.

29. A computer program product having a non-transitory computer readable medium, said computer program product providing a system for preoperatively predicting the optical properties of a pseudophakic eye of a patient with an IOL of known power and geometry, said computer program product comprising means for carrying out all the steps of the method according to claim 26.

* * * * *

UNITED STATES PATENT AND TRADEMARK OFFICE
CERTIFICATE OF CORRECTION

PATENT NO.       : 8,657,445 B2                                              Page 1 of 1
APPLICATION NO. : 13/063326
DATED            : February 25, 2014
INVENTOR(S)      : Thomas Olsen It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 287 days.

Signed and Sealed this

Twenty-ninth Day of September, 2015

Michelle K. Lee
*Director of the United States Patent and Trademark Office*